United States Patent
Ng et al.

(10) Patent No.: US 12,338,296 B2
(45) Date of Patent: Jun. 24, 2025

(54) PEPTIDES AND COMPOUNDS THAT BIND TO ELONGATION INITIATION FACTOR 4E

(71) Applicant: AGENCY FOR SCIENCE, TECHNOLOGY AND RESEARCH, Singapore (SG)

(72) Inventors: Simon Ng, Singapore (SG); Christopher John Brown, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 855 days.

(21) Appl. No.: 17/436,118

(22) PCT Filed: Mar. 30, 2020

(86) PCT No.: PCT/SG2020/050192
§ 371 (c)(1),
(2) Date: Sep. 3, 2021

(87) PCT Pub. No.: WO2020/204828
PCT Pub. Date: Oct. 8, 2020

(65) Prior Publication Data
US 2022/0242906 A1 Aug. 4, 2022

(30) Foreign Application Priority Data
Mar. 29, 2019 (SG) .............. 10201902892R

(51) Int. Cl.
*A61K 38/00* (2006.01)
*A61P 25/00* (2006.01)
*A61P 31/00* (2006.01)
*A61P 35/00* (2006.01)
*C07K 7/06* (2006.01)

(52) U.S. Cl.
CPC ............... *C07K 7/06* (2013.01); *A61P 25/00* (2018.01); *A61P 31/00* (2018.01); *A61P 35/00* (2018.01); *A61K 38/00* (2013.01)

(58) Field of Classification Search
CPC .......... A61K 38/00; A61P 25/00; A61P 31/00; A61P 35/00; C07K 7/06
See application file for complete search history.

(56) References Cited

U.S. PATENT DOCUMENTS

2018/0354993 A1* 12/2018 Urban ............... A61P 31/20

FOREIGN PATENT DOCUMENTS

| WO | WO-2010/138084 A1 | 12/2010 | |
|---|---|---|---|
| WO | WO-2011/136744 A1 | 11/2011 | |
| WO | WO-2018024827 A1 * | 2/2018 | ....... G01N 33/56961 |
| WO | WO-2018/073394 A1 | 4/2018 | |

OTHER PUBLICATIONS

Search Report and Written Opinion in International Application No. PCT/SG2020/050192 dated Aug. 11, 2020, 11 pages.
First Office Action in CN Application No. 202080025505.7 dated Nov. 28, 2023, 16 pages.
Extended European Search Report in EP Application No. 20782868.2 dated Apr. 28, 2023, 6 pages.
Frosi et al., "Development of a Novel Peptide Aptamer that Interacts With the eIF4E Capped-mRNA binding Site Using Peptide Epitope Linker Evolution (PELE)", RSC Chemical Biology, vol. 3, No. 7, Jul. 6, 2022, 15 pages.
Second Office Action in SG Applicatioin No. 202080025505.7 dated May 25, 2024, 15 pages.

* cited by examiner

*Primary Examiner* — Aradhana Sasan
*Assistant Examiner* — Mercy H Sabila
(74) *Attorney, Agent, or Firm* — MARSHALL, GERSTEIN & BORUN LLP

(57) ABSTRACT

A peptide that binds to elongation initiation factor 4E (eIF4E) comprising the amino acid sequence $CEX_1GX_2X_3X_4X_5C$ (SEQ ID NO: 1), where $X_1$ is an amino acid selected from the group consisting of threonine (T), methionine (M) or leucine (L), $X_2$ and $X_3$ is an amino acid selected from the group consisting of phenylalanine (F), modified phenylalanine and tyrosine (Y), $X_4$ and $X_5$ is any amino acid, wherein the two cysteine residues are joined by a disulphide bond. Further, pharmaceutical compositions and uses of the peptide, and pharmaceutical compositions are provided.

13 Claims, 10 Drawing Sheets
Specification includes a Sequence Listing.

A

Ratio ≥ 5
*p*-value ≤ 0.15

| | | |
|---|---|---|
| SEQ ID NO: 39 | EE-1 | ACETGFFTGCG |
| SEQ ID NO: 2 | EE-2 | ACEMGFFQDCG |
| SEQ ID NO: 40 | EE-3 | ACELGYYNDCG |
| SEQ ID NO: 41 | EE-4 | ACETGFFLKCG |
| SEQ ID NO: 42 | EE-5 | ACELGFYRLCG |
| SEQ ID NO: 43 | EE-6 | ACETGFFLRCG |
| SEQ ID NO: 44 | EE-7 | ACETGYFSQCG |
| SEQ ID NO: 45 | Peptide 45 | ACIHSPTSLCG |
| SEQ ID NO: 46 | EE-8 | ACETGFYKTCG |
| SEQ ID NO: 47 | EE-9 | ACEMGYFGNCG |

Consensus Motif

Peptide Interaction Motif

B

EE-02 bound eIF4E m⁷GDP bound eIF4E

Non Interacting Residues

Pocket 2

Pocket 3

Pocket 1

Pocket 4

PEPTIDES AND COMPOUNDS THAT BIND TO ELONGATION INITIATION FACTOR 4E

CROSS-REFERENCE TO RELATED APPLICATIONS

This application claims the benefit of priority of Singapore application No. 10201902892R, filed 29 Mar. 2019, the contents of it being hereby incorporated by reference in its entirety for all purposes.

INCORPORATION BY REFERENCE

This patent application incorporates by reference in its entirety the Sequence Listing identified as "9869SG5793 corrected sequence listing_ST25", which is an ASCII text file in computer readable form (CRF). The text file was created Mar. 9, 2022 and is 11.7 kilobytes in size.

FIELD OF THE INVENTION

This invention relates to cell proliferation-inhibiting peptides. In particular, the present invention relates to peptides that bind to elongation factor 4E (eIF4E).

BACKGROUND OF THE INVENTION

The most frequently occurring cancer mutations are found in signal transductions pathways feeding into the translational machinery. These include well studied and validated oncogenes such as MYC, RAS and PIK3C. Furthermore a broad range of translation initiation factors are commonly found to be either amplified or misregulated in tumors. eIF4E (elongation initiation factor 4E) is frequently misregulated and overexpressed in a large majority of cancers, and is critically involved in the up-regulation of a large group of oncogenic related proteins (such as VEGF and c-MYC).

eIF4E plays an essential role in initiation of translation by interacting directly with the 5'cap structure of mRNAs. All nuclear transcribed mRNA possess this 5'cap structure (m7GTP), which consists of guanosine, methylated at position 7, connected by a 5'-to-5' triphosphate bridge to the first nucleotide of the mRNA. A vast majority of eukaryotic mRNAs including oncogenes are translated in an eIF4E cap dependent manner and overexpression of eIF4E lead to an increase in the translation of these genes. As such, eIF4E activity levels need to be controlled to prevent uncontrolled proliferation.

One of the ways in which eIF4E levels and activity is regulated is through the regulation of eIF4E activity by eIF4E binding proteins (4E-BPs). The 4E-BPs negatively regulate eIF4E and share a common binding motif to eIF4G, which they use to bind eIF4E directly and competitively displace the eIF4G scaffold protein. The displacement of eIF4G impairs the assembly of the eIF4F complex on the 5' cap structure and hinders cap-dependent translation.

There is therefore a need to identify eIF4E binding agents possessing a distinct mechanism of action from that described above to circumvent emerging mechanisms of resistance that have been reported for compounds that target signalling pathways upstream of eIF4E involved in regulating protein synthesis. There is also a need to develop eIF4E binding agents for use in anti-cancer therapy.

SUMMARY

In one aspect, there is provided a peptide comprising the amino acid sequence $CEX_1GX_2X_3X_4X_5C$ (SEQ ID NO: 1), wherein $X_1$ is an amino acid selected from the group consisting of threonine (T), methionine (M) or leucine (L); wherein $X_2$ is an amino acid selected from the group consisting of a hydrophobic amino acid, an aromatic amino acid, a modified hydrophobic amino acid and a modified aromatic amino acid; wherein $X_3$ is an amino acid selected from the group consisting of a hydrophobic amino acid, an aromatic amino acid, a modified hydrophobic amino acid and a modified aromatic amino acid; wherein $X_4$ is any amino acid; wherein $X_5$ is any amino acid; wherein the two cysteine residues are joined by a disulphide bond; and wherein the peptide binds to elongation initiation factor 4E (eIF4E).

In another aspect, there is provided a peptide as described herein for use as a medicament.

In another aspect, there is provided a peptide as described herein for use in treating a condition associated with dysregulated cap-dependent translation.

In another aspect, there is provided a pharmaceutical composition comprising the peptide as described herein and a pharmaceutically acceptable carrier.

In another aspect, there is provided a use of the peptide as described herein, or the pharmaceutical composition as described herein in the manufacture of a medicament for treating a condition associated with dysregulated cap-dependent translation.

In another aspect, there is provided a method of treating a condition associated with dysregulated cap-dependent translation in a subject in need thereof, comprising the administering the peptide as described herein, or the pharmaceutical composition as described herein to the subject.

Definitions

As used herein, the terms "protein" or "peptide" refer to a polymeric form of amino acids. Proteins are understood to comprise more amino acids than peptides and a "protein" typically comprises at least about 60 amino acids while peptides typically comprise from 2 to about 60 amino acids. The amino acids in a protein or peptide may exist in either the D or L configuration or a combination of the two configurations and may be chemically or biochemically modified. Modification of the amino acids may take place at the side chains or at the peptide bond linking the amino acids. The peptide bonds (—CONH—) may be modified to change the properties of the peptide bond. The peptide may also be chemically modified by the addition of covalently bound chemical groups such as biotin, thiol, cysteine, amide, carboxyl, linear or branched alkyl, primary or secondary amines, lipids, phospholipids, fatty acids, cholesterol etc. These chemical groups may be added to the peptide at the N-terminal and/or C-terminal end or within the peptide. A peptide may also be modified by the addition of one or more additional bonds within the peptide between the N- and C-terminals, such as a disulphide bond. The amine group at the N-terminal may also be chemically modified, for example by the additional of a cap by acetylation.

The term "amino acid" as used herein refers to a molecule that comprises amine (—NH$_2$) and carboxyl (—COOH) functional groups and a side chain. Amino acids may be encoded by triplet codons of nucleic acids (canonical amino acids) or by variant codons (non-canonical amino acids). Amino acids may be characterized as α-amino acids or β-amino acids. In α-amino acids, the amine and carboxylic groups are attached to the first carbon. In β-amino acids, the amine and carboxyl groups are attached to adjacent carbons. Amino acids may also be characterized as D-amino acids (where the stereogenic carbon alpha to the amino group has the D-configuration) or L-amino acids (where the stereogenic carbon alpha to the amino group has the L-configuration). Amino acids may also be classified based on their properties of their side chains. For example, amino acids may be classified as acidic, basic, polar, hydrophobic or aromatic and an amino acid may fall into one or more categories. Aromatic amino acids include phenylalanine, tryptophan, tyrosine, and histidine. Hydrophobic amino acids include glycine (Gly), alanine (Ala), valine (Val), leucine (Leu), isoleucine (Ile), proline (Pro), phenylalanine (Phe), methionine (Met), and tryptophan (Trp). Polar amino acids include serine (Ser), threonine (Thr), cysteine (Cys), asparagine (Asn), glutamine (Gln), and tyrosine (Tyr). Basic amino acids include arginine (Arg), lysine (Lys), and histidine (His) and acidic amino acids include aspartic acid or aspartate (Asp) and glutamic acid or glutamate (Glu).

Amino acids as used herein may be naturally occurring, non-naturally occurring or synthetic. Amino acids as used herein may also be modified by substituting one or more groups on the side chains.

TABLE 1

Amino acids

| Amino Acid | Three-letter abbreviation | One-letter abbreviation |
| --- | --- | --- |
| Alanine | ala | A |
| Arginine | arg | R |
| Asparagine | asn | N |
| Aspartic acid | asp | D |
| Cysteine | cys | C |
| Glutamine | gln | Q |
| Glutamic acid | glu | E |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |
| Selenocysteine | — | — |
| Pyrrolysine | — | — |
| Sarcosine | sar | — |
| Beta-alanine | β-ala | bA/βA |
| Norleucine | nle | — |
| Cyclobutylalanine | cba | — |

As used herein, the term "modified", "modification" or grammatical variants thereof in the context of a modified amino acid refers to an amino acid wherein one or more groups on the side chain is substituted. The one or more groups may be substituted with alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamino, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$.

As used herein, the term "alkyl group" includes within its meaning monovalent ("alkyl") and divalent ("alkylene") straight chain or branched chain saturated aliphatic groups having from 1 to 10 carbon atoms, eg, 1, 2, 3, 4, 5, 6, 7, 8, 9, or 10 carbon atoms.

The term "alkenyl group" includes within its meaning monovalent ("alkenyl") and divalent ("alkenylene") straight or branched chain unsaturated aliphatic hydrocarbon groups having from 2 to 10 carbon atoms, eg, 2, 3, 4, 5, 6, 7, 8, 9, or 10 carbon atoms and having at least one double bond, of either E, Z, cis or trans stereochemistry where applicable, anywhere in the alkyl chain.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, eg, 3, 4, 5, 6, 7, 8, 9, or 10 carbon atoms.

The term "cycloalkenyl" as used herein, refers to cyclic unsaturated aliphatic groups and includes within its meaning monovalent ("cycloalkenyl") and divalent ("cycloalkenylene"), monocyclic, bicyclic, polycyclic or fused polycyclic hydrocarbon radicals having from 3 to 10 carbon atoms and having at least one double bond, of either E, Z, cis or trans stereochemistry where applicable, anywhere in the alkyl chain. Examples of cycloalkenyl groups include but are not limited to cyclopropenyl, cyclopentenyl, cyclohexenyl, and the like.

The term "heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 3 to 10 ring atoms wherein 1 to 5 ring atoms are heteroatoms selected from O, N, NH, or S. Examples include pyrrolidinyl, piperidinyl, quinuclidinyl, azetidinyl, morpholinyl, tetrahydrothiophenyl, tetrahydrofuranyl, tetrahydropyranyl, and the like.

The term "heterocycloalkenyl" as used herein, includes within its meaning monovalent ("heterocycloalkenyl") and divalent ("heterocycloalkenylene"), saturated, monocyclic, bicyclic, polycyclic or fused polycyclic hydrocarbon radicals having from 3 to 10 ring atoms and having at least 1 double bond, wherein from 1 to 5 ring atoms are heteroatoms selected from O, N, NH or S.

The term "heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having 6 to 20 atoms wherein 1 to 6 atoms are heteroatoms selected from O, N, NH and S.

The term "heteroatom" or variants such as "hetero-" as used herein refers to 0, N, NH and S.

The term "alkoxy" as used herein refers to straight chain or branched alkyloxy groups.

The term "amino" as used herein in the context of substitution refers to groups of the form —NR$_a$R$_b$ wherein R$_a$ and R$_b$ are individually selected from the group including but not limited to hydrogen, optionally substituted alkyl, optionally substituted alkenyl, optionally substituted alkynyl, and optionally substituted aryl groups.

The term "aromatic group", or variants such as "aryl" or "arylene" as used herein refers to monovalent ("aryl") and divalent ("arylene") single, polynuclear, conjugated and fused residues of aromatic hydrocarbons having from 6 to 10 carbon atoms.

The term "aralkyl" as used herein, includes within its meaning monovalent ("aryl") and divalent ("arylene"), single, polynuclear, conjugated and fused aromatic hydrocarbon radicals attached to divalent, saturated, straight and branched chain alkylene radicals.

The term "heteroaralkyl" as used herein, includes within its meaning monovalent ("heteroaryl") and divalent ("heteroarylene"), single, polynuclear, conjugated and fused aromatic hydrocarbon radicals attached to divalent saturated, straight and branched chain alkylene radicals.

The term "halogen" or variants such as "halide" or "halo" as used herein refers to fluorine, chlorine, bromine, iodine and cyanohalide.

The term "equilibrium dissociation constant" or "dissociation constant" ($K_d$) as used herein is a measure of the strength of binding between two molecules, for example, a protein and its ligand. The smaller the dissociation constant, the more tightly bound the two molecules are and the higher the affinity between the two molecules.

As used herein, the term "inhibit" in the context of activity of eIF4E means that the level of biological activity of eIF4E is disrupted, reduced or absent compared to the level of activity of eIF4E that is not inhibited.

The terms "macrocycle" and "macrocyclic" in the context of a peptide or protein refer to a cyclic peptide which is a polypeptide chain which contain a circular sequence of bonds. This can be through a connection between the amino and carboxyl ends of the peptide, for example in cyclosporin; a connection between the amino end and a side chain, for example in bacitracin; the carboxyl end and a side chain, for example in colistin; or two side chains or more complicated arrangements, for example in amanitin.

The term "pharmaceutical composition" as used herein refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

As used herein, the term "pharmaceutically acceptable carrier" refers to media generally accepted in the art for the delivery of biologically active agents, i.e. the disclosed inhibitor alone or in combination with any of the disclosed compounds in the context of the specification, to mammals, e.g. humans. Such carriers are generally formulated according to a number of factors well within the purview of those of ordinary skill in the art to determine and account for. These include, without limitation, the type and nature of the active agent, being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Non-limiting examples of a pharmaceutically acceptable carrier are hyaluronic acid and salts thereof, and microspheres (including, but not limited to, poly(D,L)-lactide-co-glycolic acid copolymer (PLGA), poly(L-lactic acid) (PLA), poly(caprolactone) (PCL) and bovine serum albumin (BSA)). The term "cancer" as used herein refers to any of a number of diseases that are characterized by uncontrolled, abnormal proliferation of cells, the ability of affected cells to spread locally or through the bloodstream and lymphatic system to other parts of the body (i.e., metastases), as well as any of a number of characteristic structural and/or molecular features. Examples of cancers include but are not limited to breast, bronchial, colon, colorectal, liver, lung, prostate, ovarian, brain, pancreatic, head and neck, stomach and bladder cancers, non-Hodgkin's lymphomas, leukaemias, neuroblastomas, melanomas, gliomas, or glioblastomas.

BRIEF DESCRIPTION OF THE DRAWINGS

The invention will be better understood with reference to the detailed description when considered in conjunction with the non-limiting examples and the accompanying drawings, in which:

FIG. 1A shows a unique and novel motif was identified that interacts with eIF4E, which contrasts with the peptide interaction motif that screening of linear 12mer libraries usually isolates. FIG. 1B shows binding site identified using fluorescence polarization experiments. Top graph demonstrates that C7C peptides cannot displace fluorescently labelled peptide containing the peptide interaction motif. This motif is found in the protein interaction partners of eIF4E->4E-BPs(1,2 and 3) and eIF4G1. The graph below demonstrated that the C7C macrocyclic EE-02 can displace fluorescently labelled m7GTP.

FIG. 3 shows the structure of the eIF4E cap binding site in complex with or without m7GDP.

FIG. 4 shows a comparison of the structures of eIF4E bound with either EE-02 or m7GDP.

Figure 1:
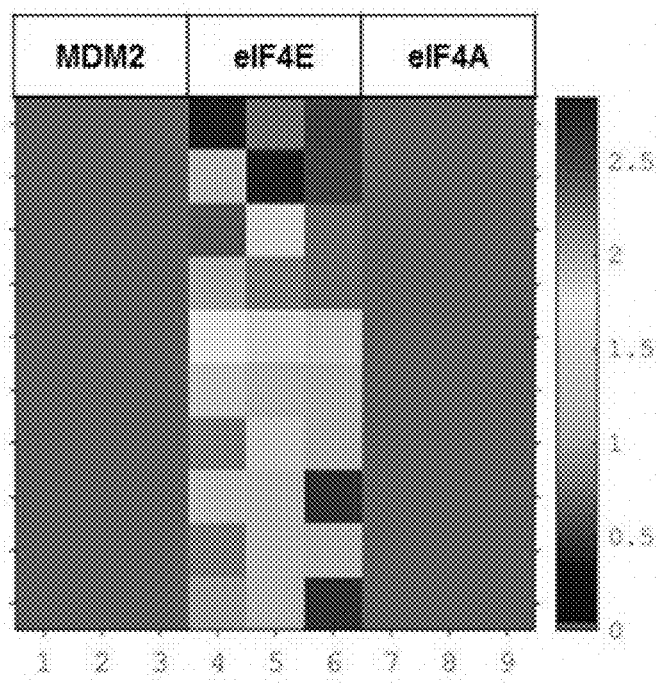
FIG. 1 shows the Next Generation Sequencing (NGS) phage sequencing results and fluorescence polarization competition experiments. NGS enhanced phage display screening against eIF4E was performed using a C7C library (commercially available from NEB). C7C=disulphide constrained cyclic peptide displayed on the pili of M13 phage.
Figure 1:
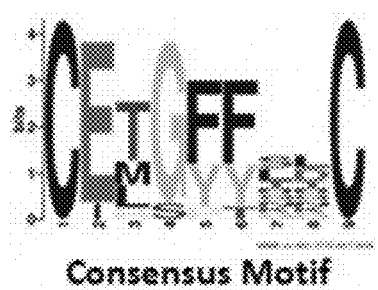
Figure 1:
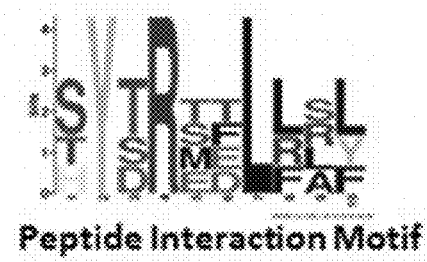
Figure 1:
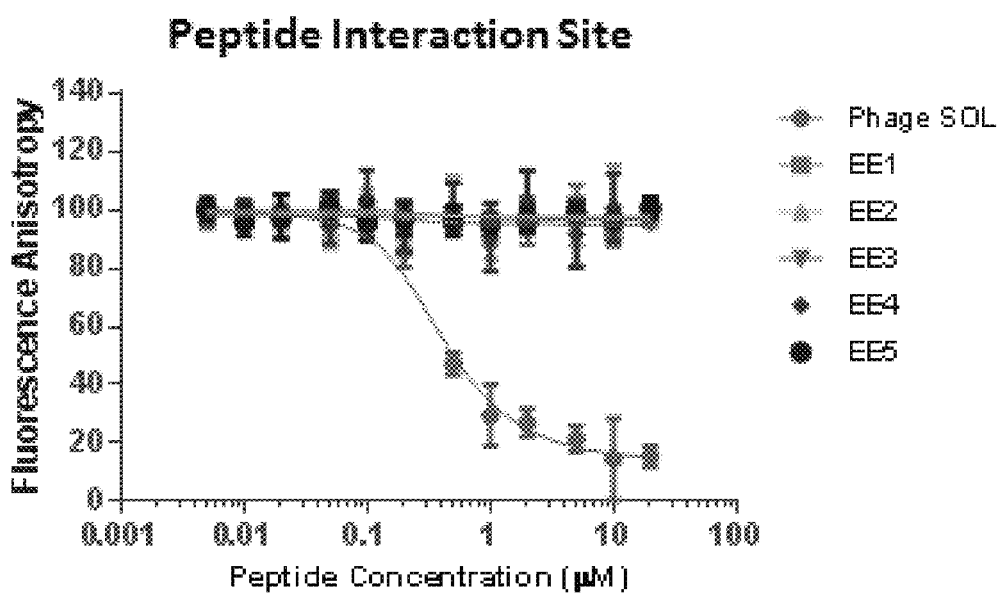
Figure 1:
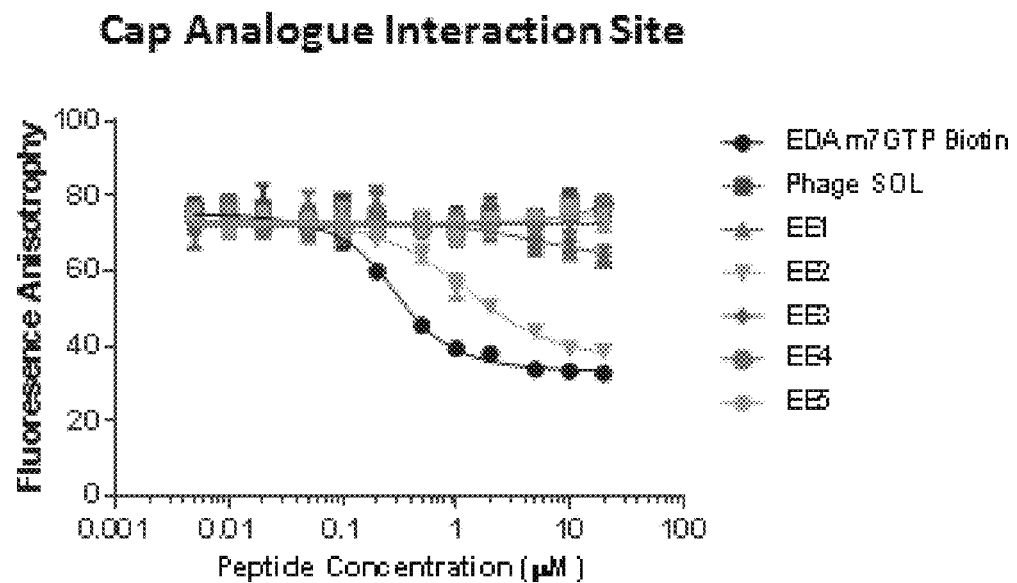

All images in the foregoing figures are based on real XTAL™ structures of EE-02 in complex with eIF4E.

DETAILED DESCRIPTION OF THE PRESENT INVENTION

In a first aspect the present invention refers to a peptide comprising the amino acid sequence $CEX_1GX_2X_3X_4X_5C$ (SEQ ID NO: 1), wherein $X_1$ is an amino acid selected from the group consisting of threonine (T), methionine (M) or leucine (L); wherein $X_2$ is an amino acid selected from the group consisting a hydrophobic amino acid, an aromatic amino acid, a modified hydrophobic amino acid and a modified aromatic amino acid; wherein $X_3$ is an amino acid selected from the group consisting of a hydrophobic amino acid, an aromatic amino acid, a modified hydrophobic amino acid and a modified aromatic amino acid; wherein $X_4$ is any amino acid; wherein $X_5$ is any amino acid; wherein the two cysteine residues are joined by a disulphide bond; and wherein the peptide binds to elongation initiation factor 4E (eIF4E).

In one embodiment, the peptide comprises the amino acid sequence $CEX_1GFFX_4X_5C$ (SEQ ID NO: 13).

The peptides of the present invention may be isolated from a cell or from a reaction vessel by methods that are generally known in the art. The peptides of the present invention may also be purified by methods that are generally known in the art.

In some embodiments, the peptides of the present invention may be chemically synthesized prior to isolation or purification. For example, the peptides of the present invention may be synthesized by fluorenylmethyloxycarbonyl protecting group strategy (FMOC) solid phase chemical synthesis. This is followed by oxidation mediated by iodine to form the disulphide bond to constrain the peptide.

In one embodiment, the peptide binds to eIF4E at the mRNA 5' cap-binding site. The peptide binds to the mRNA 5' cap-binding site of eIF4E with high affinity. In one embodiment, the peptide binds to the mRNA 5' cap-binding site with a dissociation constant ($K_d$) of less than about 250 nM, less than about 200 nM, less than about 150 nM, less than about 100 nM, less than about 50 nM. In one embodiment, the peptide binds to eIF4E at the mRNA 5' cap-binding site with a $K_d$ of less than 100 nM.

The peptide may interact with the 5' cap-binding site via a different mechanism or mode than the way that the cap analogue (m7GDP) interacts with the 5' cap-binding site.

In one embodiment, the peptide binds to eIF4E cap-binding site with a different conformation than m7GDP. In another embodiment, binding of the peptide to eIF4E disrupts binding of the cap-analogue to the cap binding site. This in turn inhibits the activity of eIF4E.

In one embodiment, the peptide binds to eIF4E in an open conformation. "Open conformation" refers to the conformations of phenylalanine at positions 102 and 56 (W102 and W56) when they are not interacting with m7GDP and are swung out of the binding site. In contrast, "closed conformation" refers to the conformation of W102 and W56 when they have swung back into the cap binding site with m7GDP clamped between them.

In one embodiment, binding of the peptide to eIF4E inhibits eIF4E activity.

It will generally be understood that the disulphide bond between the two cysteine residues cyclizes the peptide.

It will be understood that the cyclized peptides of the present invention interact with eIF4E and when the disulphide bond is reduced the interaction is abrogated. The peptides of the present invention represent the key motif responsible for this interaction with eIF4E and the necessity for the peptide to be constrained.

The peptide comprising the amino acid sequence $CEX_1GX_2X_3X_4X_5C$ (SEQ ID NO: 1) of the present invention may in one embodiment be methionine (M) at position $X_1$. In another embodiment, $X_2$ and $X_3$ are independently selected from the group consisting of tyrosine (Y), phenylalanine (F) or modified phenylalanine.

Modified phenylalanine refers to a phenylalanine wherein one or more groups on the aromatic ring is substituted.

In another embodiment, $X_4$ and $X_5$ are independently glutamine (Q), aspartic acid (D), alanine (A), lysine (K), glycine (G) or leucine (L).

In yet another embodiment, $X_5$ is aspartic acid (D). In yet another embodiment, $X_5$ is D-aspartic acid or L-aspartic acid.

In some embodiments, the peptide may comprise one or more additional amino acid residues at the N-terminal and/or C-terminal. These one or more additional amino acid residues may be from or part of a phage on which the peptide is displayed. In one embodiment, the peptide comprises an additional alanine residue at the N-terminal and an additional glycine residue at the C-terminal. The alanine and glycine residues are the non-random parts of the phage that exist outside the random section that the phage library is consisted of.

In one embodiment of the invention, the peptide comprises the amino acid sequence selected from the group consisting of ACEMGFFQDCG (SEQ ID NO: 2), CEMGFFQDCG (SEQ ID NO: 3), ACEMGFFADCG (SEQ ID NO: 4), ACEMGFFKDCG (SEQ ID NO: 5), ACEMGFFLDCG (SEQ ID NO: 6). CEMGFFADC (SEQ ID NO:7), ACEMGYFQDCG (SEQ ID NO: 28), and ACEMGFYQDCG (SEQ ID NO: 32).

In another embodiment, the peptide consists of the amino acid sequence selected from the group consisting of ACEMGFFQDCG (SEQ ID NO: 2), CEMGFFQDCG (SEQ ID NO: 3), ACEMGFFADCG (SEQ ID NO: 4), ACEMGFFKDCG (SEQ ID NO: 5), ACEMGFFLDCG (SEQ ID NO: 6), CEMGFFADC (SEQ ID NO: 7), ACEMGYFQDCG (SEQ ID NO: 28), and ACEMGFYQDCG (SEQ ID NO: 32).

In a further embodiment, the peptide consists of the amino acid sequence CEMGFFADC (SEQ ID NO: 7).

The peptides of the present invention may be conjugated to one or more additional compounds. In one embodiment, the peptide is conjugated to one or more additional peptides.

In some embodiment, the one or more additional peptides is a cell penetrating peptide. A cell penetrating peptide (CPP) is a peptide that facilitates cellular uptake of the peptide. CPPs may be classified as synthetic, chimeric, or protein-derived or may be classified as cationic, hydrophobic or amphipathic. Examples of cell penetrating peptides include but are not limited to poly-arginine, trans-activating transcriptional activator (TAT), transportan and penetratin.

The present invention further relates to a peptide described herein for use as a medicament.

In one embodiment, the peptide described herein is for use in treating a condition associated with dysregulated cap-dependent translation.

The present invention also provides a pharmaceutical composition comprising the peptide as described herein.

The present invention further provides a use of the peptide, or the pharmaceutical composition as described herein in the manufacture of a medicament for treating a condition associated with dysregulated cap-dependent translation.

In one embodiment, dysregulated cap-dependent translation is a result of aberrant eIF4E expression or aberrant eIF4E activity.

In some embodiments, aberrant eIF4E expression is overexpression of eIF4E. In other embodiments, aberrant eIF4E activity is an increase of eIF4E activity above physiological levels. It will generally be understood that overexpression of eIF4E means that the expression of eIF4E is increased compared to normal physiological expression levels. It will also be generally understood that an increase in eIF4E activity can be mediated by increased phosphorylation of 4E-BP1.

In one embodiment, the condition associated with eIF4E overexpression is cancer.

In another embodiment, the condition associated with dysregulated cap-dependent translation is an infectious disease that hijacks cap-dependent translation. Examples of such diseases include but are not limited to influenza as well as viral diseases caused by coronaviruses.

In yet another embodiment, the condition associated with dysregulated cap-dependent translation is fragile X syndrome or autism.

The present invention also provides a vector comprising a nucleic acid sequence encoding the peptide as described here. The present invention also provides a host cell transfected with the vector as described herein wherein the host cell expresses the peptide as described herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Methods

Phage Display Method and Fluorescence Competition Experiments

Fluorescence Anisotropy Assays and $K_d$ Determination.

General Assay Design

Purified eIF4E was titrated against either 50 nM carboxyfluorescein (FAM) labelled tracer peptide (KKRYSRD-FLLALQK-(FAM)) (SEQ ID NO: 8) or 50 nM fluorescein labelled m$^7$GTP-6-FAM. The $K_d$s (dissociation constants) for both the tracer peptide and FAM labelled m$^7$GTP were determined by fitting their respective experimental titrations to a 1:1 binding model using the equation below:

$$r = r_o + (r_b - r_o) \times \frac{(K_d + [L]_t + [P]_t) - \sqrt{k_d + [L]_t + [P]_t)^2 - 4[L]_t[P]_t}}{2[L]_t}$$

where [P] is the protein concentration, [L] is the labeled peptide concentration, r is the anisotropy measured, $r_0$ is the anisotropy of the free peptide, $r_b$ is the anisotropy of the eIF4E-tracer peptide complex, $[L]_t$ is the total FAM labeled peptide concentration, and $[P]_t$ is the total eIF4E concentration. The determined $K_d$ determined for the interaction of the tracer peptide with eIF4E was 50.3 nM and that for m$^7$GTP-6-FAM was 149.0 nM. Both were used later for subsequent $K_d$ determination in competition experiments.

Apparent $K_d$ values were then determined for a variety of molecules via competitive anisotropy experiments.

Assessment of Binding at 4E:4G Site

Titrations were carried out with the concentration of eIF4E constant at 200 nM and the labeled peptide at 50 nM. The competing molecules were then titrated against the complex of the FAM labeled peptide and eIF4E. Apparent $K_d$ values were determined by fitting the experimental data to the equations shown below:

$$r = r_o + (r_b + r_o) \times \frac{2\sqrt{(d^2 - 3e)} \cos(\theta/3) - 9}{3K_{d1} + 2\sqrt{(d^2 - 3e)} \cos(\theta/3) - d}$$

$$d = K_{d1} + K_{d2} + [L]_{st} + [L]_t - [P]_t$$

$$e = ([L]_t - [P]_t)K_{d1} + ([L]_{st} - [P]_t)K_{d2} + K_{d1}K_{d2}$$

$$f = -K_{d1}K_{d2}[P]_t$$

$$\theta = ar \cos\left[\frac{-2d^3 + 9de - 27f}{2\sqrt{(d^2 - 3e)^3}}\right]$$

$[L]_{st}$ and $[L]_t$ denote labeled ligand and total unlabeled ligand input concentrations, respectively. $K_{d2}$ is the dissociation constant of the interaction between the unlabelled ligand and the protein. In all competitive types of experiments, it is assumed that $[P]_t > [L]_{st}$, otherwise considerable amounts of free labeled ligand would always be present and would interfere with measurements. $K_{d1}$ is the apparent $K_d$ for the labeled peptide used in the respective experiment. The tracer peptide was dissolved in DMSO at 1 mM and diluted into experimental buffer. Readings were carried out with a Envision Multi-label Reader (PerkinElmer). Experiments were carried out in PBS (2.7 mM KCl, 137 mM NaCl, 10 mM Na$_2$HPO$_4$ and 2 mM KH$_2$PO$_4$ (pH 7.4)), 3% DMS (v/v) and 0.1;% Tween 20 buffer. All titrations were carried out in triplicate. Curve-fitting was carried out using Prism 4.0 (GraphPad).

Cap Analogue Binding Assessment

Titrations were carded out with the concentration of eIF4E constant at 250 nM and the labeled m7GTP at 50 nM. The competing molecules were then titrated against the complex of the FAM labeled m7GTP and eIF4E. Apparent $K_d$ values were determined by fitting the experimental data to the equations shown below:

$$r = r_o + (r_b + r_o) \times \frac{2\sqrt{(d^2 - 3e)} \cos(\theta/3) - 9}{3K_{d1} + 2\sqrt{(d^2 - 3e)} \cos(\theta/3) - d}$$

$$d = K_{d1} + K_{d2} + [L]_{st} + [L]_t - [P]_t$$

$$e = ([L]_t - [P]_t)K_{d1} + ([L]_{st} - [P]_t)K_{d2} + K_{d1}K_{d2}$$

$$f = -K_{d1}K_{d2}[P]_t$$

$$\theta = ar \cos\left[\frac{-2d^3 + 9de - 27f}{2\sqrt{(d^2 - 3e)^3}}\right]$$

$[L]_{st}$ and $[L]_t$ denote labeled ligand and total unlabeled ligand input concentrations, respectively. $K_{d2}$ is the dissociation constant of the interaction between the unlabelled ligand and the protein. In all competitive types of experiments, it is assumed that $[P]_t > [L]_{st}$, otherwise considerable amounts of free labeled ligand would always be present and would interfere with measurements. $K_{d1}$ is the apparent $K_d$ for the labeled peptide used in the respective experiment. The FAM labelled m7GTP was provided at 1 mM in Tris-HCL pH 7.5 (Jena Biosciences) and diluted into experimental buffer. Readings were carried out with a Envision Multi-label Reader (PerkinElmer). Experiments were carried out in PBS (2.7 mM KCl, 137 mM NaCl, 10 mM NaHPO$_4$ and 2 mM KHPO$_4$ (pH 7.4)), 3% DMSO (v/v) and 0.1% Tween 20 buffer. All titrations were carried out in triplicate. Curve-fitting was carried out using Prism 4.0 (GraphPad).

NGS Enhanced Phage Display
Selection of C7C Disulphide Constrained Phage Library Against eIF4E
Phage Library The C7C phage library was purchased from New England Biolabs. The library is a combinatorial library of random peptides with a disulfide constrained loop, fused to a minor coat protein (pIII) of M13 phage. The displayed peptide, in the form AC-X$_7$-CGGGS (X=random amino acid) (SEQ ID NO: 9), is expressed at the N-terminus of pIII. The two cysteines spontaneously form a disulphide bridge under oxidising condition to constrain the peptide sequence. The library consists of approximately 1×10$^9$ electroporated (i.e., unique) sequences.

eIF4E Immobilization and Phage Selection

A 96-well polystyrene plate was coated with a solution of streptavidin (150 µl per well, 20 µg/ml and incubated overnight at 4° C. 3. The coating solution was then removed. The wells on the 96-well plate were then washed 4 times with 200 µl of binding buffer (50 mM Tris-HCl, 150 mM NaCl (pH 7.4)). After washing, wells were then loaded with 150 µl of biotin labelled protein (5-10 mg/ml in binding buffer). Streptavidin control wells were loaded only with 150 µl of binding buffer. The 96 well plate was then incubated for 15 mins at room temperature, and then their contents decanted. Wells were then washes 4 times with 200 µl of binding buffer. After washing, wells were blocked with 200 µl of blocking buffer ((50 mM Tris-HCl, 150 mM NaCl (pH 7.4). 0.01% BSA (w/v), 0.1% Tween20 (v/v)) for 30 mins at room temperature. In parallel, the phage library was then prepared in blocking buffer with 1×10$^{12}$ pfu/ml, and also incubated at room temperature for 30 minutes. Blocking buffer was then decanted from the 96 well plate, and 100 µl of phage library distributed between the wells approx. 10$^{11}$ pfu per well). The plate was then incubated at room temperature for 1 hour. Non-bound phage were then removed by pipetting from the individual wells. Welles were then washed 8 times with 200 µl of washing buffer. Bound phage were then incubated with 100 µl of elution buffer (0.2 M glycine-HCl, pH 2.2+0.1% (w/v) BSA) for 9 minutes at room temperature. Supernatant containing eluted phage were then individually transferred to separate tubes containing 15 µl of neutralization buffer (1 M Tris-HCl, pH 9.1).

Phage Amplification and M13 DNA Isolation

Dilute overnight culture of E. coli (strain ER 2738) 100-fold and distribute 3 ml of the culture to each 15 ml culture tube. Incubate cultures at 37° C. with shaking at 230 rpm for 4 to 4.5 hours. After incubation, centrifuge the tubes for 15 min at 4000 rpm at 4° C. to pellet the bacteria cells. To precipitate the phage, decant the supernatant from each tube into a separate 5 ml falcon tube containing MP buffer (30 µl, 100×) and vortex. Load 700 µl of the precipitated phage solution to a separate Qiagen spin column and centrifuge for 30 seconds at 8000 rpm. Discard the resulting flow-through. After this step, apply 700 µl of buffer PB to each spin column and centrifuge at 8000 rpm for 30 s. Again discard the flow-through and repeat this step. Upon completion of this step add 700 µl Buffer PE to each spin column. Spin each column at 8000 rpm for 30 s and discard flow-through from collection tube. Repeat the centrifugation step but extending the spin to 2 mins to remove any residual PE buffer. Transfer the spin columns to fresh 1.5 ml Eppendorf tubes. Elute the DNA adding EB buffer (50 µl) to each column and then waiting 1 min before centrifuging for 30 s at 800 rpm. For further details on buffers and procedure consult the m13 QIAprep Spin M13 Kit manual (Qiagen, Ltd).

MP Buffer Recipe
1. Dissolve 3.3 g citric acid monohydrate in 3 ml high-purity water at room temperature (21° C.)
2. Incubate the solution by stirring at 200 rpm for 5 min
3. Filter the solution through a 0.2 m sterile filter using a syringe to give a final volume of 6 ml Buffer MP.

Barcoding and Library Amplification 15 reverse barcoded primers were designed with adapters compatible with Illumina sequencing sequencing. The library DNA was subjected to PCR amplification with the barcoded primers flanking the variable region. Each eluate of ssM13 phage DNA was uniquely coded. Briefly, the library DNA (15 samples, 50 ng each) was amplified in a total volume of 25 µL with 1× Phusion® buffer, 200 µM each dNTPs, 1.5 mM $MgCl_2$, 0.5 µM forward primer, 0.5 µM reverse barcoded primer, and one unit Phusion® High-Fidelity DNA Polymerase. PCR was performed using the following thermo cycler program: 95° C. for 30 s, followed by 25 cycles of 95° C. for 10 s, 60.5° C. for 15 s and 72° C. for 30 s, and then a final extension at 72° C. for 5 min before holding at 4° C. The dsDNA fragments from the PCR were quantified by running at 2% (w/v) agarose gel in Tris-Borate-EDTA buffer at 100 volts for ~45 min using a low molecular weight DNA ladder as a standard (NEB, #N3233S). The dsDNA fragments (15 samples, 40 ng per sample) were pooled together and purified on E-Gel® SizeSelect™ 2% agarose gel (Invitrogen, #G6610-02). The desired band corresponding to 121 bp with reference to the ladder was collected with RNAse-free water. DNA concentration of purified DNA was determined using PicoGeen (Thermofisher) according to manufacturer's instructions.

DNA Template Preparation and Illumina Sequencing (NextSEQ)

Sequencing was performed by AXIL Scientific. The pooled DNA was hybridized to an Illumina chip, bridge amplified and then sequenced using Illumina technology. Both the NextSeq® 500 Mid Output Kit (150 cycles) (cat FC-404-1001) and the NextSeq® 500/550 Mid Output Kit v2 (150 cycles) (cat FC-404-2001) were used to sequence the reads in both the forward (F) and reverse (R) directions. FASTQ files were processed using paired-end analysis using internally developed python scripts.

Differential Enrichment and Sequence Logo Generation

FASTQ files were analyzed and parsed to separate sequences via their relevant barcodes into their respective selections. The frequency of each unique peptide sequence encoded by the variable domain was then determined and normalized by the total number of sequences in the selection. This was repeated for each replicate e.g. eIF4E replicate 1 to 3 and Streptavidin control 1 to 3. Sequences not observed in a specific replicate were assigned a normalized frequency of zero. The enrichment ratio of each sequence was determined by dividing the mean normalized frequency of a particular sequence (derived from the replicate set for that selection) and dived by that in the control set of replicates. Since the denominator must not be a zero when taking the ratio, sequences that did not occur in all three replicates are assigned with an arbitrary value (e.g. 0.0001) before calculating the ratio. Significance (p-value) of the ratio was assessed using unequal variances Student t-test (Welch test). Heat maps were then generated for arbitrary determined values for p-value and the enrichment ration. Typical values used were p-value <0.1 and ratio >5.0. Sequences were ranked by their enrichment value in the heat map. The heat map identified sequences isolated from a particular selection that increased significantly in abundance against sequences isolated from the control selection (or group of non-related selections). Sequence logos were generated using WebLogo (Berkeley) from the enriched sequences.

Tryptophan Quenching Experiments

Tryptophan quenching experiments were performed using an EnVision® multiplate reader with black matte 96-well plates. Samples (100 µl) were prepared with 1 µM purified eIF4E against a range of concentrations for the following compounds: $m^7GTP$, PHAGESOL (KKRYSRDQLVAL) (SEQ ID NO: 10) or EE-02. Concentrations tested ranged from 0.01-20 µM. Samples were excited with UV light at 290 nm to minimise contribution from tyrosine fluorescence. Tryptophan was measured at an emission wavelength of 355 nm.

Crystallization of eIF4E:EE-02

Crystallization

The eIF4E:EE-02 complex was crystallized by vapour diffusion using the sitting drop method. Crystallization drops contained eIF4E and EE-02 at concentrations of 150 µM and 300 µM respectively. Sitting drops were set up in 48 well Intelli-Plates (Hampton research) with 1 µl of the protein sample mixed with 1 µl of the mother-well solution. Crystals grew over a period of one week in 0.2 M Ammonium sulphate 0.1 M Tris-sodium acetate pH 4.6 and 25% PEG 4000. For X-ray data collection at 100 K, crystals were transferred to an equivalent mother liquor solution containing 20% (v/v) glycerol and then flash frozen in liquid nitrogen.

Data Collection and Refinement

The data was collected at the Australian synchrotron on beamline MX1 using a CCD detector. The crystal diffracted to a resolution of 2.35 Å and was integrated and scaled using XDS. The initial phases of the binary complexed crystals of eIF4E were solved by molecular replacement with the program PHASER using the human eIF4E structure with waters and other bound components removed (PDB accession code: 4BEA) as a search model. The starting model was subjected to rigid body refinement and followed by iterative cycles of manual model building in Coot and restrained refinement in Refmac 6.0.

General Methods

Expression, Refolding, and Purification of eIF4E (Used for Fluorescence Polarization (FP), Surface Plasmon Resonance (SPR) and Crystallography Experiments)

Rossetta pLysS competent bacteria were transformed with the pET11d expression plasmid containing the full-length eIF4E clone. Both materials were provided by Cyclacel Ltd., Dundee. The cells expressing the full-length eIF4E construct were grown in LB medium at 37° C. to an $OD_{600}$ of ~0.6 and eIF4E induction was started with 1 mM IPTG. The culture was immediately placed in a shaker-incubator for 3 h at 37° C. Cells were harvested by centrifugation and the cell pellets were resuspended in 50 mM Tris pH 8.0, 10% sucrose, and were then sonicated.

The sonicated sample was centrifuged for 10 min at 17,000 g at 4° C. The resulting pellet was resuspended in Tris/Triton buffer (50 mM Tris pH 8.0, 2 mM EDTA, 100 mM NaCl, 0.5% Triton X-100). The sample was then centrifuged at 25,000 g for 15 min at 4° C. and the pellet was resuspended in Tris/Triton buffer. After re-centrifugation, the remaining pellet was solubilised in 6 M guanidinium hydrochloride, 50 mM Hepes-KOH pH 7.6, 5 mM DTT. The protein concentration of the sample was then adjusted to 1 mg/mL.

The denatured protein was refolded via a 1/10 dilution into refolding buffer consisting of 20 mM Hepes-KOH, 100 mM KCl and 1 mM DTT. The refolded protein was concentrated and desalted using an Amersham PD10 column into refolding buffer. The eIF4E protein sample was run over a monoQ column and eluted with a 1 M KCl gradient. eIF4E eluted as a sharp peak at a ~0.3M KCl.

Surface Plasmon Resonance (for Structural Activity Relationship (SAR) Tables)

For stock peptide solutions, the compounds were dissolved in 100% DMSO to a concentration of 10 mM; further dilutions of the peptide stock solutions into DMSO and/or running buffer were performed immediately prior to analysis. Running buffer consisted of 10 mM Hepes pH 7.6, 0.15 M NaCl, and 0.1% Tween20. Stock/DMSO diluted peptide solutions were diluted into 1.03× running buffer to make a peptide solution with 3% DMSO final concentration. Working concentrations of peptide were reached with further dilution of samples into running buffer which contained 3% DMSO. Surface Plasmon resonance experiments were performed on a Biacore T100 machine.

Pure eIF4E was immnobilized on a CM5 sensor chip. The CM5 chip was conditioned with a 6 s injection of 100 mM HCL, followed by a 6 s injection of 0.1% SDS and completed with a 6 s injection of 50 mM NaOH at a flow rate of 100 µl/min. Activation of the sensor chip surface was performed with a mixture of NHS (115 mg ml$^{-1}$) and EDC (750 mg ml$^{-1}$) for 7 min at 10 µl min$^{-1}$. Purified eIF4E was diluted with 10 mM sodium acetate buffer (pH 5.0) to a final concentration of 0.5 µM with m$^7$GTP present in a 2:1 ratio in order to stabilize eIF4E. The amount of eIF4E immobilized on the activated surface was controlled by altering the contact time of the protein solution and was approximately 1000 RU. After the immobilization of the protein, a 7-min injection (at 10 µl min$^{-1}$) of 1 M ethanolamine (pH 8.5) was used to quench excess active succinimide ester groups.

Six buffer blanks were first injected to equilibrate the instrument fully and then a solvent correction curve was performed followed by a further two blank injections. The solvent correction curve was setup by adding varying amount of 100% DMSO to 1.03× running buffer to generate a range of DMSO solutions (3.8%, 3.6%, 3.4%, 3.2%, 3%, 2.85%, 2.7% and 2.5% respectively). Using a flow rate of 50 µl/min, compounds were injected for 60 s and dissociation was monitored for 180 s. The data collection rate was 10 Hz. $K_d$s were determined using the BiaEvaluation software (Biacore) and calculated from both the response of the eIF4E coated CM5 chips at equilibrium and also kinetically from the dissociation and association phase data for each of the peptides. Both the equilibrium and kinetic data were fitted to 1:1 binding models. Each individual peptide $K_d$ was determined from three separate titrations. Within each titration at least two concentration points were duplicated to ensure stability and robustness of the chip surface.

GST Affinity Purification of eIF4E for Biotinylation

Full length eIF4E were ligated into the GST fusion expression vector pGEX-4 (GE Lifesciences) via a BAMH1 and NDE1 double digest. BL21 DE3 competent bacteria were then transformed with the GST tagged eIF4E fusion constructs. The cells expressing the GST fusion constructs were grown in LB medium at 37° C. to an OD600 of ~0.6 and induction was carried out with 1 mM at room temperature. Cells were harvested by centrifugation and the cell pellets were resuspended in 50 mM Tris pH 8.0, 10% sucrose and then sonicated. The sonicated sample was centrifuged for 60 mins at 17,000 g at 4° C. The supernatant was applied to a 5 ml FF GST column (Amersham) pre-equilibrated in wash buffer (Phosphate Buffered Saline, 2.7 mM KCL and 137 mM NaCL, pH 7.4) with 1 mM DTT. The column was then further washed by 6 volumes of wash buffer. eIF4E was then purified from the column by cleavage with Precission (GE Lifesciences) protease. 50 units of thrombin protease, in one column volume of PBS with 1 mM DTT buffer, were injected onto the column. The cleavage reaction was allowed to proceed overnight at 4° C. The cleaved protein was then eluted of the column with wash buffer. Protein fractions were analyzed with SDS page gel and concentrated using a Centricon (10 kDa MWCO) concentrator, Millipore. eIF4E protein samples were then dialyzed into a buffer solution containing of 20 mM Hepes-KOH, 100 mM KCl and 1 mM DTT. The eIF4E protein sample was then run over a monoQ column and eluted with a 1 M KCl gradient. eIF4E eluted as a sharp peak at a ~0.3M KCl. Protein concentration was determined using UV absorbance.

Sortase Mediated Biotinylation of eIF4E for Immobilisation n Phage Display

A biotin tag was incorporated onto GS-eIF4E using sortase mediated ligation. The following reagents were combined in a volume of 1000 µls: 40 µM GS-eIF4E, 5 µM SrtA61-206-His6 (8M), 200 µM, Biotin-KGGGLPET-GG-OHse(Ac)-amide in ligation buffer (50 mM Tris, 1500 mM NaCl, 10 mM TCEP (pH 8.0)). The sample was incubated at room temperature for 4 hours. 2 µl of the sample was analysed for labelling efficiency by SDS-PAGE gel. After analysis, the reaction sample was then purified to remove all reaction components except eIF4E. The sample was re-suspended with 50 µl pre-washed magnetic His-Tag beads (Qiagen) and incubated for 5 mins at room temperature on a roller. 7. Place the tube on magnet for 2 min, then transfer the supernatant containing the biotinylated protein to a fresh Eppendorf tube. Dialyze the biotinylated protein using slide-A-Lyzer cassette (10 k MWCO) against 2 L PBS (4 hours), then change buffer to 50 mM Tris, 150 mM NaCl, (pH 7.4) and dialyze overnight. Measure protein concentration. Aliquot and flash freeze protein sample.

Results

A Novel Macrocyclic Peptide that Binds eIF4E at the Cap-Binding Site

A phage display library was panned against N-terminally biotinylated eIF4E. The phage display library used consisted of 7 randomised amino acids constrained by a disulphide bond between two cysteine residues (ACXXXXXXXC-GGGS) (SEQ ID NO: 9), which was fused to the minor coat protein (pIII) of the M13 phage via a GGS linker. The library was commercially sourced from New England Biolabs (NEB). eIF4E was biotinylated via peptide ligation, whereby a biotin labelled peptide (biotin-LPETGG)(SEQ ID NO: 37) was fused to a N-terminal glycine on eIF4E using a sortase. eIF4E was produced with an N-terminal glycine via purification using a GST tag, and removal of the GST tag using thrombin. Biotinylated eIF4E was immobilised on streptavidin coated plates.

Next generation sequencing (NGS) enhanced phage display was performed by performing 3× selections against eIF4E and 3× control selections (against both Mdm2 and eIF4A). Selections were performed as described in the Methods. Phage were isolated, amplified and sequenced using Illumina NextSEQ technology (see Methods). Data was analysed using in house python scripts and identified a set of unique peptides with a novel eIF4E interaction motif (FIG. 1).

The consensus motif identified consisted of C-E-(T/M/L)-G-F-F-X-X-C(SEQ ID NO: 11). X denoting any amino acid. A parallel NGS enhance phage selection was performed with a phage library consisting of a randomised 12mer linear peptide (NEB) against eIF4E. However, this library only identified the well eIF4E interaction binding motif that interacts at the eif4g binding site on eIF4E. (YXRXXLΦ, Φ=any hydrophobic amino acid) (SEQ ID NO: 12).

From these initial results it was predicted the new peptide motif might interact with eIF4E either via a different binding pose at the eIF4G binding site, or at the cap-binding site or elsewhere on the protein. The binding site was initially delineated on eIF4E by using two types of competitive fluorescence polarization experiments, one of which utilised a FAM labelled cap-analogue and the other that used a FAM labelled eIF4G1 derived peptide (FIG. 1). These experiments confirmed that EE-02 (ACEMGFFQDCG) (SEQ ID NO: 2) (FIG. 1) was the most potent peptide out of the set identified and confirmed that this novel interaction motif disrupted binding of the cap-analogue to eIF4E.

The structure of EE_02 is significantly different to that of the cap analogue, which consists of a guanine triphosphate molecule that possesses a methyl substitution at the N7 position of the guanine ring. This immediately suggested that the macrocyclic peptide may interact with the cap-binding site via a very different mechanism.

Figure 2:
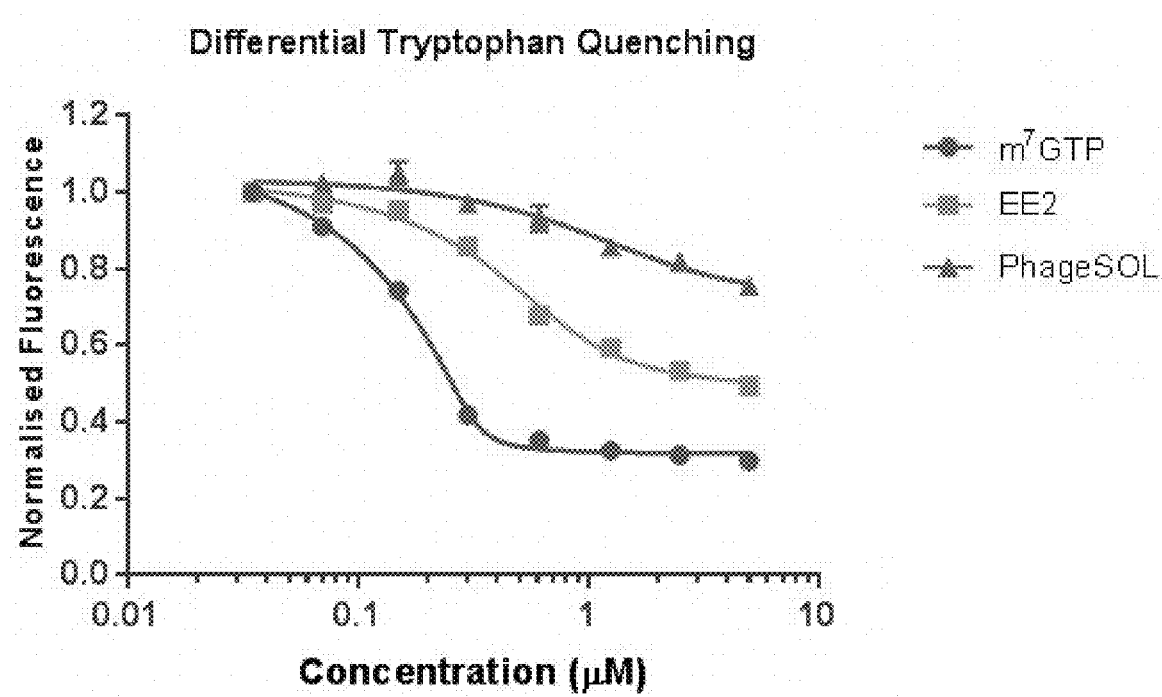
FIG. 2 shows tryptophan quenching experiments. The graph demonstrates how m7GTP and EE-02 have very distinct profiles highlighting that they may bind with different binding conformations. PHAGSOL is a phage derived peptide that was identified to interact with the eIF4G binding site on eIF4E-contains canonical peptide interaction motif.

To substantiate this hypotheses tryptophan quenching experiments were performed, where either EE-02, m7GTP or an eIF4G1 derived peptide were titrated against eIF4E (FIG. 2).

The PhageSol peptide produced significantly lower amounts of tryptophan quenching compared to the other titrants. This result was expected as only one tryptophan residue (W73) is located within the proximity of the eIF4G binding site, especially in comparison to m7GTP/m7GDP which binds at the cap-binding sites and intercalates between two tryptophan residues (W56 and W102) and causes significantly more quenching as a result. However, EE-02 which also binds at the cap-binding sites produces a significantly different profile to m7GTP/m7GDP. This difference suggests that the EE-02 interaction with eIF4E is occurring through a different mode, and potentially could be allosteric in how it is affecting the cap-binding site.

Figure 3A:
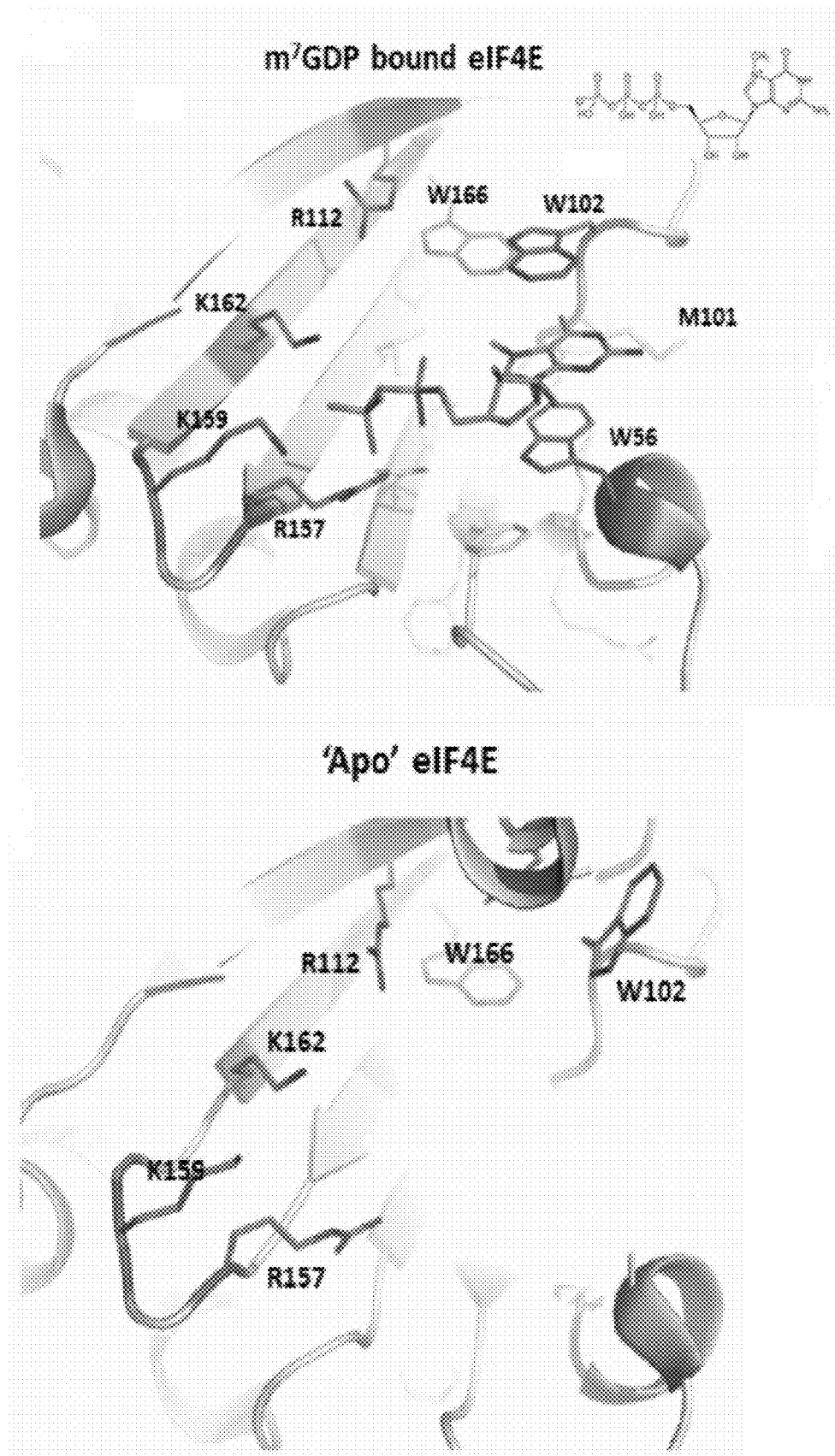
FIG. 3A shows comparison of the m7GDP bound eIF4E structure (left) with the unbound structure (right). When $m^7GDP$ is bound, the indole side chains of W56 and W102 intercalate the guanine ring of the nucleotide. E103 of eIF4E forms 2 hydrogen bonds that recognise the guanine ring. Additionally, the methyl group present on the N7 of the guanine ring induces the formation of a quaternary amine, which imparts a delocalised positive charge on the ring system. This results in the formation of cation-π interactions with W56 and W102, further stabilising the bound conformation. The diphosphate tail of m7GDP is recognised and forms electrostatic interactions with R157, K159 and K162. The residue R112 further recognises the phosphate moieties via several structured water molecules. This conformation is termed the 'closed' conformation. When eIF4E is unbound, significant conformational changes occur around the region responsible for binding the N7 methyl substituted guanine moiety. These changes are the rotation of W102, the movement of the W56 containing loop and rotation of E103 out of the cap-binding site. This conformation is termed the "open' state.
Figure 3B:
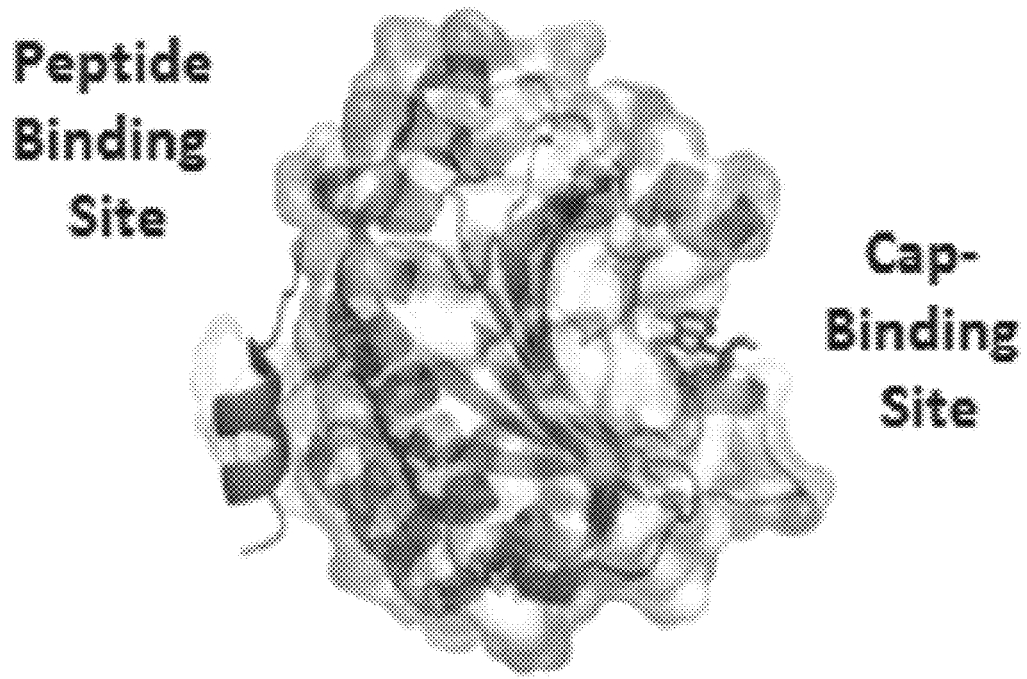
FIG. 3B show the locations of the canonical peptide and cap binding sites on eIF4E.
Figure 3C:
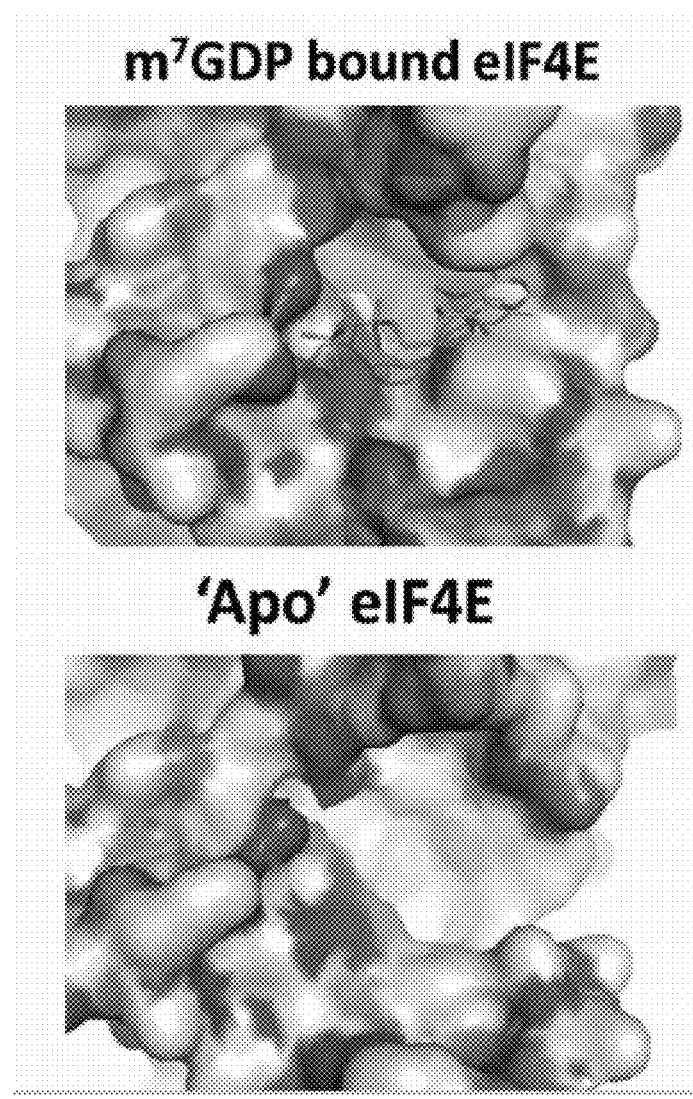
FIG. 3C shows the surface representation of m7GDP bound eIF4E and 'apo' eIF4E structures demonstrating the distinct structural differences in the shape and size of the cap-binding site between the two states.
Figure 4A:
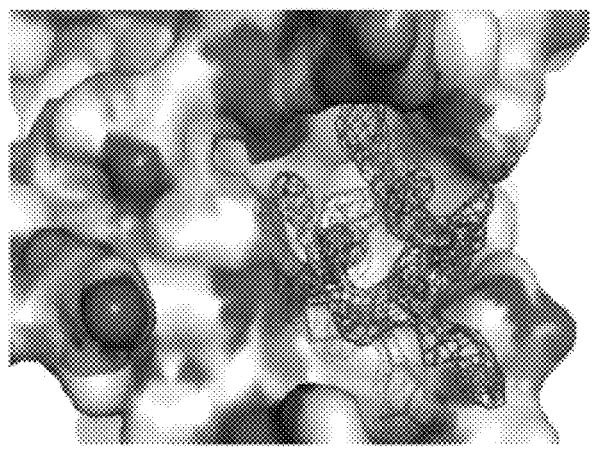
FIG. 4A shows the surface representation of EE-02 bound eIF4E demonstrating the similarity of the shape and size of its cap-binding site with that of "apo" eIF4E, and highlighting the differences with the cap-site of m7GDP bound eIF4E.
Figure 4A:
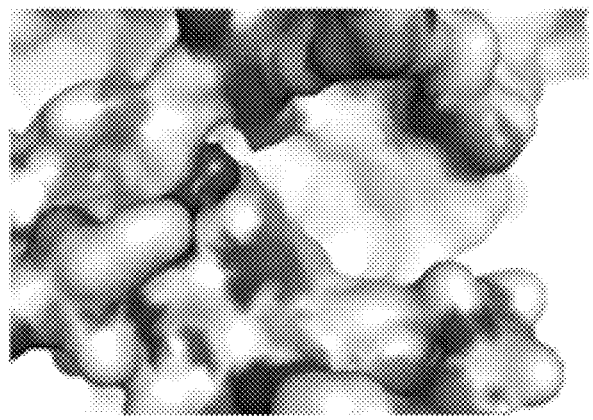
Figure 4A:
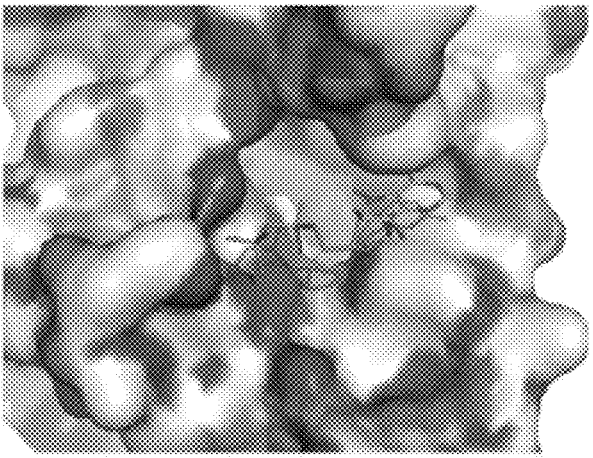
Figure 4B:
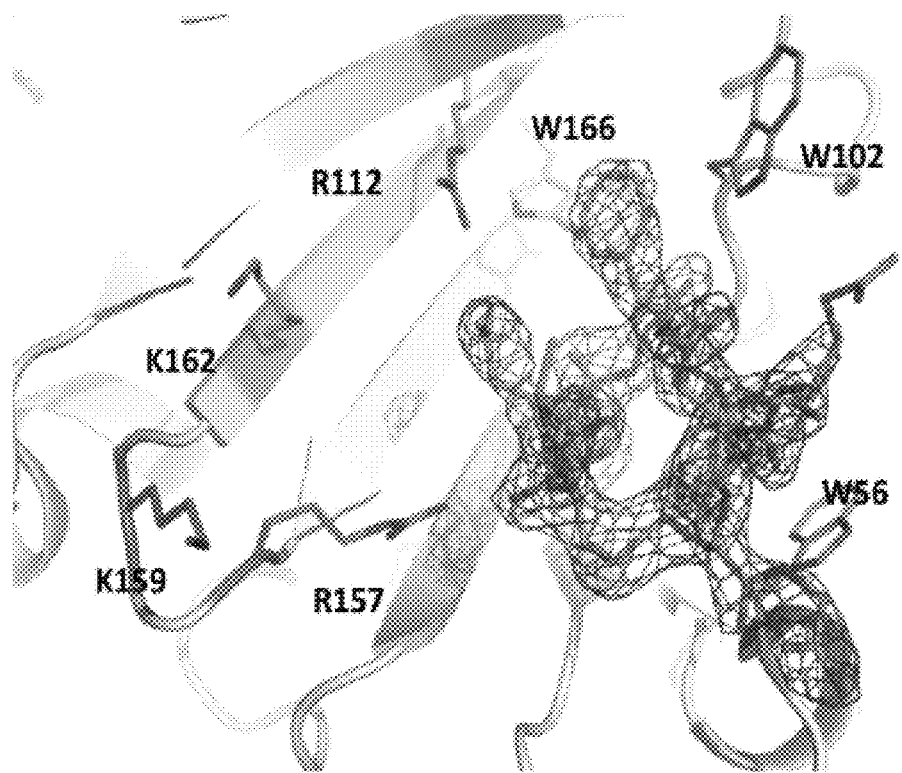
FIG. 4B shows the comparison of the EE-02 bound eIF4E structure with the m7GDP bound structure. EE-02 binds eIF4E in a conformation very similar to the 'apo' structure of eIF4E. E3 of EE-02 interacts directly with R112, M4 forms a hydrogen bond with S92 of eIF4E at the back of the cap-binding site, whilst residues F6 and F7 form hydrophobic interactions. The residues, W56 and W102, responsible for recognising the guanine ring system are rotated out of the cap-binding site. E103 that forms h-bonds with m7GDP has also swung out of the cap-binding site and is not involve in interaction of EE-02 with eIF4E. Additionally, EE-02 does not directly interact with the residues that form the diphosphate binding pocket (R157, K159 and K162) in contrast to m7GDP.
Figure 4B:
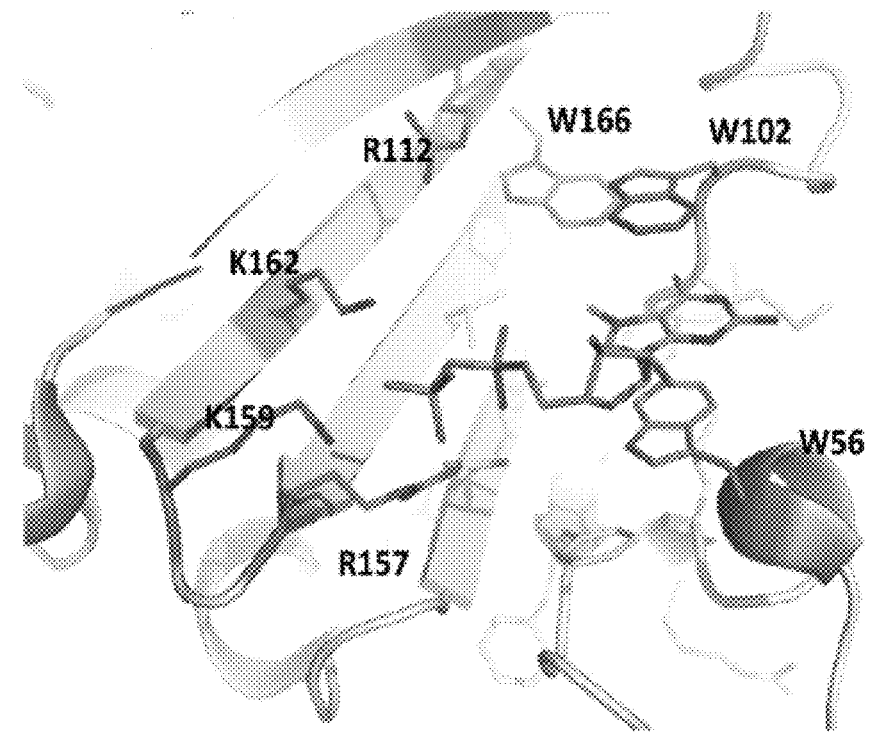

To address this question, structural studies were pursued and the crystal structure of EE-02 bound to eIF4E was successfully solved (FIGS. 3 and 4).

Structural studies revealed that EE-02 interacts with the cap-binding site directly and does not intercalate between the tryptophan rings. This result explains the different profiles observed in the tryptophan quenching experiments. Additionally, EE-02 macrocyclic binds eIF4E without mimicking the phosphate tail or cation-π interactions made by m7GDP (FIGS. 3, 4 and 5).

Figure 5:
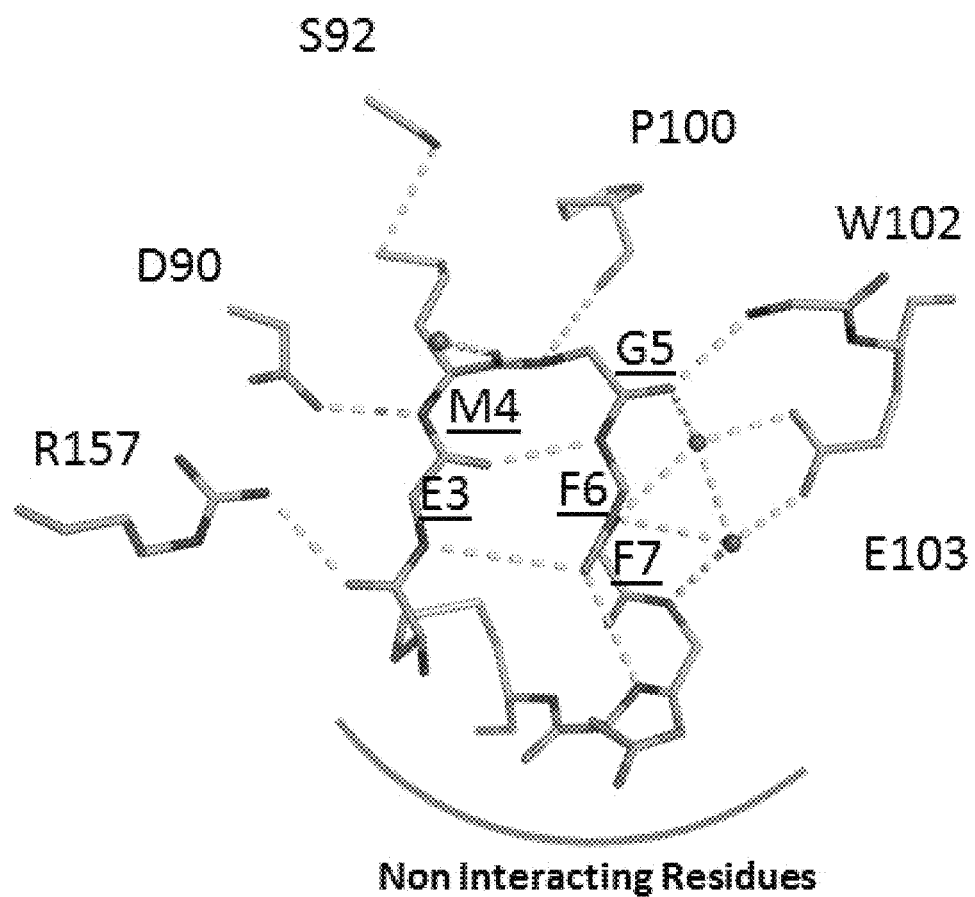
FIG. 5 shows key interactions made by conserved residues of the interaction motif identified by NGS phage sequencing in the crystal structure. Key hydrogen bonds made by EE-02 with eIF4E and itself are also highlighted.
Figure 5:
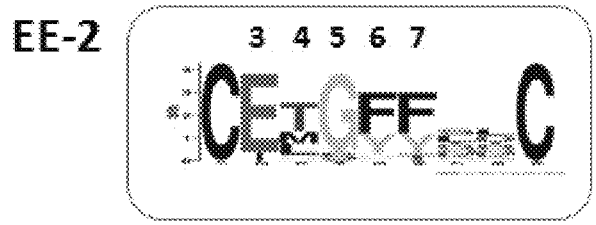
Figure 5:
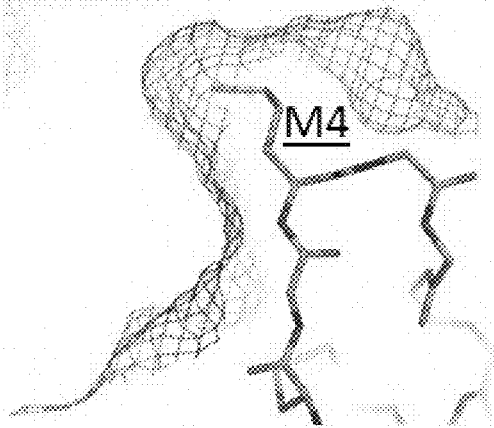
Figure 5:
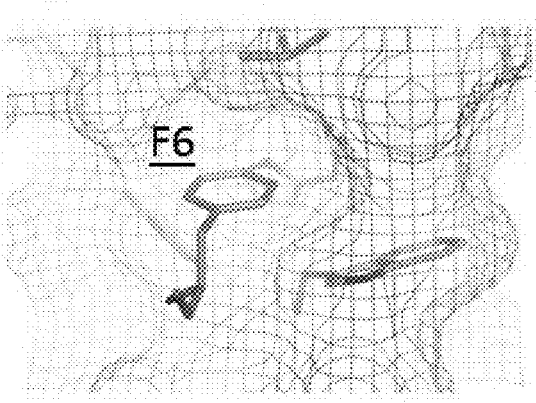
Figure 5:
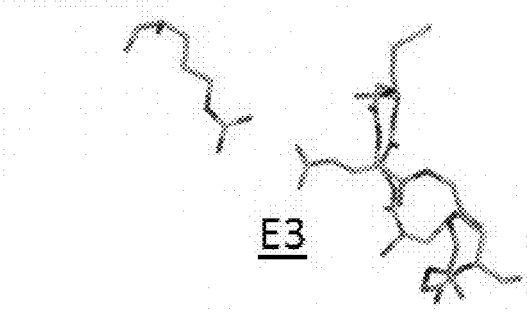
Figure 5:
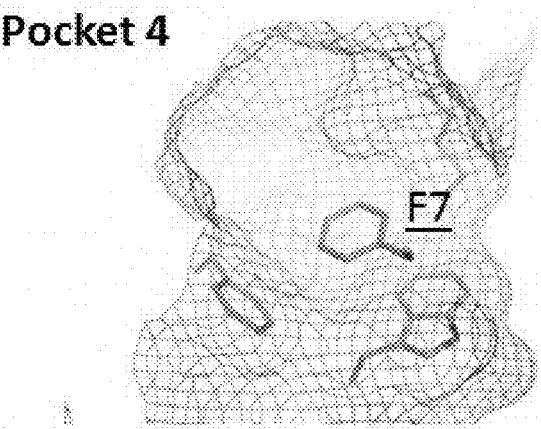

EE-02 interacts with eIF4E via 4 distinct pockets (FIG. 5). The macrocyclic itself forms a β-hairpin turn into the cap-binding site that enable the projection of residues E3, E4, F6 and F7 into the corresponding pockets shown in FIG. 5.

Alanine scanning mutagenesis was also performed on EE-02 to confirm the critical interactions identified in the crystal structure (Table 2).

TABLE 2

Alanine scanning mutagenesis of EE-02.

| Name | N-term | 1 | 2 | 3 | 4 | 5 | 6 | 7 | 8 | 9 | 10 | 11 | C-term | mean KD (nM) | SD of KD | SEQ ID NO. |
|---|---|---|---|---|---|---|---|---|---|---|---|---|---|---|---|---|
| EE-2  | amine | A | C | E | M | G | F | F | Q | D | C | G | amide | 207    | 57 | 2  |
| EE-2A | amine | A | C | A | M | G | F | F | Q | D | C | G | amide | 11000  |    | 14 |
| EE-2B | amine | A | C | E | A | G | F | F | Q | D | C | G | amide | >50000 |    | 15 |
| EE-2C | amine | A | C | E | M | A | F | F | Q | D | C | G | amide | 32000  |    | 16 |
| EE-2D | amine | A | C | E | M | G | A | F | Q | D | G | G | amide | >50000 |    | 17 |
| EE-2E | amine | A | C | E | M | G | F | A | Q | D | C | G | amide | >50000 |    | 18 |
| EE-2F | amine | A | C | E | M | G | F | F | A | D | C | G | amide | 167    | 38 | 4  |
| EE-2G | amine | A | C | E | M | G | F | F | Q | A | C | G | amide | 530    | 0  | 19 |

$K_d$ were determined using surface plasmon resonance (SPR) as described in Methods. Alanine scanning confirmed that residues E3, M4, G5, F6 and F7 were all critical for binding to eIF4E. The sensitivity of G5 to substitution highlights its important in allowing the formation of a 0-hairpin with the correct geometry in the binding pocket. Substitution of Q8 with A did not affect binding. However, replacement of D9 with A causes a two-fold decrease in binding.

TABLE 3

Targeted mutagenesis on position E3 and M4 of EE-02

| Name | N-term | 1 | 2 | 3 | 4 | 5 | 6 | 7 | 8 | 9 | 10 | 11 | C-term | mean KD (nM) | SD of KD | SEQ ID NO. |
|---|---|---|---|---|---|---|---|---|---|---|---|---|---|---|---|---|
| EE-2  | amine | A | C | E | M   | G | F | F | Q | D | C | G | amide | 207   | 57 | 2  |
| EE-19 | amine | A | C | D | M   | G | F | F | Q | D | C | G | amide | 26000 |    | 20 |
| EE-20 | amine | A | C | E | I   | G | F | F | Q | D | C | G | amide | 1600  |    | 21 |
| EE-21 | amine | A | C | E | L   | G | F | F | Q | D | C | G | amide | 2500  |    | 22 |
| EE-22 | amine | A | C | E | Nle | G | F | F | Q | D | C | G | amide | 520   |    | 23 |
| EE-23 | amine | A | C | E | Cba | G | F | F | Q | D | C | G | amide | 35000 |    | 24 |

E4 could not be replaced by D4 highlighting the important of correct orientation of the carboxyl group to interact with R112 of eIF4E. M4 was replaced with shorter and smaller aliphatic groups such as I and L that resulted in loss of binding. M4 was also replaced with the non-natural aliphatic amino acids norleucine and cyclobutylalanine, which are similar in size to methionine. However, the $K_d$s determined for these molecules still decreased against eIF4E, highlighting the importance of the sulphur atom interaction with S92.

TABLE 4

Targeted mutagenesis of residue G5

| Name | N-term | 1 | 2 | 3 | 4 | 5 | 6 | 7 | 8 | 9 | 10 | 11 | C-term | mean KD (nM) | SD of KD | SEQ ID NO. |
|---|---|---|---|---|---|---|---|---|---|---|---|---|---|---|---|---|
| EE-2 | amine | A | C | E | M | G | F | F | Q | D | C | G | amide | 207 | 57 | 2 |
| EE-27 | amine | A | C | E | M | bA | F | F | Q | D | C | G | amide | >50000 | | 25 |
| EE-28 | amine | A | C | E | M | Sar | F | F | Q | D | C | G | amide | 4200 | | 26 |
| EE-29 | amine | A | C | E | M | P | F | F | Q | D | C | G | amide | >50000 | | 27 |

G5 was replaced with different amino acids (beta-alanine (bA), Sarcosine (Sar), P) to explore different stereo-chemical restraints around this position. All resulted in dramatic decreases in macrocyclic binding to eIF4E, further highlighting the role of G5 in allowing the beta hairpin to form and to orientate the key interacting residues into their most optimal positions to bind eIF4E.

TABLE 5

Targeted mutagenesis of positions F6 and F7 in EE-02

| Name | N-term | 1 | 2 | 3 | 4 | 5 | 6 | 7 | 8 | 9 | 10 | 11 | C-term | mean KD (nM) | SD of KD | SEQ ID NO. |
|---|---|---|---|---|---|---|---|---|---|---|---|---|---|---|---|---|
| EE-2 | amine | A | C | E | M | G | F | F | Q | D | C | G | amide | 207 | 57 | 2 |
| EE-30 | amine | A | C | E | M | G | Y | F | Q | D | C | G | amide | 85 | 31 | 28 |
| EE-31 | amine | A | C | E | M | G | W | F | Q | D | C | G | amide | 5900 | | 29 |
| EE-33 | amine | A | C | E | M | G | L | F | Q | D | C | G | amide | >50000 | | 30 |
| EE-34 | amine | A | C | E | M | G | F | L | Q | D | C | G | amide | >50000 | | 31 |
| EE-35 | amine | A | C | E | M | G | F | Y | Q | D | C | G | amide | 137 | 6 | 32 |
| EE-36 | amine | A | C | E | M | G | F | W | Q | D | C | G | amide | 2600 | | 33 |
| EE-37 | amine | A | C | E | M | G | Y | Y | Q | D | C | G | amide | 350 | | 34 |
| EE-38 | amine | A | C | E | M | G | L | L | Q | D | C | G | amide | >50000 | | 35 |

Binding to eIF4E can be incrementally improved by exploring ring substituents on F6 and F7. Replacement of F6 with Y6 or F7 with Y7 produced two molecules that bound more tightly than EE-02 (EE-30 and EE-35, respectively). These results that these positions can be explored further to generate better binding analogues.

TABLE 6

Target mutagenesis of position Q8 in EE-02

| Name | N-term | 1 | 2 | 3 | 4 | 5 | 6 | 7 | 8 | 9 | 10 | 11 | C-term | mean KD (nM) | SD of KD | Fold change | SEQ ID NO. |
|---|---|---|---|---|---|---|---|---|---|---|---|---|---|---|---|---|---|
| EE-2 | amine | A | C | E | M | G | F | F | Q | D | C | G | amide | 207 | 57 | 1 | 2 |
| EE-2F | amine | A | C | E | M | G | F | F | A | D | C | G | amide | 167 | 38 | 0.8 | 4 |
| EE-39 | amine | A | C | E | M | G | F | F | K | D | C | G | amide | 109 | 12 | 0.5 | 5 |
| EE-40 | amine | A | C | E | M | G | F | F | G | D | C | G | amide | 400 | | 1.9 | 36 |
| EE-41 | amine | A | C | E | M | G | F | F | L | D | C | G | amide | 190 | | 0.9 | 37 |

Position 8 of EE-02 shows no strict preference for a particular residues. This correlates with the fact in forms no interactions with eIF4E in the crystal structure. However, the slight decrease in binding seen with the G mutation suggest that rigidification strategies at this position could improve binding via a mechanism of entropy reduction.

TABLE 7

Truncation studies on EE-02

| Name | N-term | 1 | 2 | 3 | 4 | 5 | 6 | 7 | 8 | 9 | 10 | 11 | C-term | mean KD (nM) | SD of KD | Fold change | SEQ ID NO. |
|---|---|---|---|---|---|---|---|---|---|---|---|---|---|---|---|---|---|
| EE-2 | amine | A | C | E | M | G | F | F | Q | D | C | G | amide | 207 | 57 | 1 | 2 |
| EE-2FAM | 5FAM | A | C | E | M | G | F | F | Q | D | C | G | amide | 2100 |  | 10.1 | 2 |
| EE-2G | amine | A | C | E | M | G | F | F | Q | A | C | G | amide | 530 | 0 | 2.6 | 19 |
| EE-2H | Ac |  | C | E | M | G | F | F | Q | D | C |  | amide | 1700 |  | 8.2 | 38 |
| EE-11 | Ac | A | C | E | M | G | F | F | Q | D | C | G | amide | 1000 |  | 4.9 | 2 |
| EE-12 | amine |  | C | E | M | G | F | F | Q | D | C | G | amide | 77 | 6 | 0.4 | 3 |
| EE-44 | amine |  | C | E | M | G | F | F | A | D | C |  | amide | 79 | 9 | 0.4 | 7 |

These studies were designed to find the smallest macrocyclic by molecular weight (MW) could bind eIF4E. Additionally N-terminal capping of the macrocyclics were studied to identify the effects of acetylation vs free amine upon eIF4E binding. This resulted in the identification of EE-44 were the non-library phage amino acid positions i.e. A1 and G11 could be removed, and that acetylation dramatically decreased binding of the macrocyclic. EE-44 due to its small MW and decreased size is a more suitable starting point for rationally designing macrocyclics with improved permeability.

TABLE 8

Summary of sequence listing

| Description | SEQ ID NO |
|---|---|
| CEX$_1$GX$_2$X$_3$X$_4$X$_5$C | 1 |
| EE-2 | 2 |
| EE-12 | 3 |
| EE-2F | 4 |
| EE-39 | 5 |
| EE-41 | 6 |
| EE-44 | 7 |
| FAM labelled tracer peptide | 8 |
| Phage display peptide | 9 |
| PHAGESOL | 10 |
| C-E-(T/M/L)-G-F-F-X-X-C | 11 |
| eIF4E interaction binding motif | 12 |
| CEXGFFXXC | 13 |
| EE-2A | 14 |
| EE-2B | 15 |
| EE-2C | 16 |
| EE-2D | 17 |
| EE-2E | 18 |
| EE-2G | 19 |
| EE-19 | 20 |
| EE-20 | 21 |
| EE-21 | 22 |
| EE-22 | 23 |
| EE-23 | 24 |

TABLE 8-continued

Summary of sequence listing

| Description | SEQ ID NO |
|---|---|
| EE-27 | 25 |
| EE-28 | 26 |
| EE-29 | 27 |
| EE-30 | 28 |
| EE-31 | 29 |
| EE-33 | 30 |
| EE-34 | 31 |
| EE-35 | 32 |
| EE-36 | 33 |
| EE-37 | 34 |
| EE-38 | 35 |
| EE-40 | 36 |
| Biotin-labelled peptide | 37 |
| EE-2H | 38 |
| EE-1 | 39 |
| EE-3 | 40 |
| EE-4 | 41 |
| EE-5 | 42 |
| EE-6 | 43 |
| EE-7 | 44 |
| Peptide 45 | 45 |
| EE-8 | 46 |
| EE-9 | 47 |

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A peptide comprising the amino acid sequence CEX1GX2X3X4X5C (SEQ ID NO: 1),
   wherein $X_1$ is an amino acid selected from the group consisting of threonine (T), methionine (M), and leucine (L);
   wherein $X_2$ is an amino acid selected from the group consisting of a hydrophobic amino acid, an aromatic amino acid, a modified hydrophobic amino acid, and a modified aromatic amino acid;
   wherein $X_3$ is an amino acid selected from the group consisting of a hydrophobic amino acid, an aromatic amino acid, a modified hydrophobic amino acid, and a modified aromatic amino acid;
   wherein $X_4$ is any amino acid;
   wherein $X_5$ is any amino acid;
   wherein the two cysteine residues are joined by a disulfide bond;
   wherein the peptide binds to elongation initiation factor 4E (eIF4E); and
   wherein $X_2$ and $X_3$ are independently selected from the group consisting of phenylalanine (F), tyrosine (Y) and a modified phenylalanine.

2. The peptide according to claim 1, wherein the peptide binds to eIF4E at the mRNA 5' cap-binding site.

3. The peptide according to claim 1, wherein binding of the peptide to eIF4E inhibits eIF4E activity.

4. The peptide according to claim 1, wherein the peptide binds to eIF4E in an open conformation.

5. The peptide according to claim 1, wherein $X_1$ is methionine (M).

6. The peptide according to claim 1, wherein $X_4$ and $X_5$ are independently glutamine (Q), aspartic acid (D), alanine (A), lysine (K), glycine (G), or leucine (L).

7. The peptide according to claim 1, wherein $X_5$ is D-aspartic acid or L-aspartic acid.

8. The peptide according to claim 1, wherein the peptide comprises an amino acid sequence selected from the group consisting of ACEMGFFQDCG (SEQ ID NO: 2), CEMGFFQDCG (SEQ ID NO: 3), ACEMGFFADCG (SEQ ID NO: 4), ACEMGFFKDCG (SEQ ID NO: 5), ACEMGFFLDCG (SEQ ID NO: 6), CEMGFFADC (SEQ ID NO:7), ACEMGYFQDCG (SEQ ID NO: 28), and ACEMGFYQDCG (SEQ ID NO: 32).

9. The peptide according to claim 1, wherein the peptide consists of the amino acid sequence CEMGFFADC (SEQ ID NO: 7).

10. The peptide according to claim 1, wherein the peptide is conjugated to one or more additional peptides.

11. The peptide according to claim 10, wherein the one or more additional peptides is a cell penetrating peptide.

12. The peptide according to claim 1 for use as a medicament.

13. A pharmaceutical composition comprising the peptide according to claim 1 and a pharmaceutically acceptable carrier.

* * * * *

SEQUENCE LISTING

```
<160> NUMBER OF SEQ ID NOS: 47

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide CEXGXXXXC
<220> FEATURE:
<221> NAME/KEY: MISC_FEATURE
<222> LOCATION: (3)..(3)
<223> OTHER INFORMATION: Xaa can be Threonine, Methionine or Leucine
<220> FEATURE:
<221> NAME/KEY: MISC_FEATURE
```

```
<222> LOCATION: (5)..(6)
<223> OTHER INFORMATION: Xaa can be a hydrophobic amino acid, an
      aromatic amino acid, a modified hydrophobic amino acid or a
      modified aromatic amino acid
<220> FEATURE:
<221> NAME/KEY: MISC_FEATURE
<222> LOCATION: (7)..(8)
<223> OTHER INFORMATION: Xaa can be any naturally occuring,
      non-naturally occuring or synthetic amino acid

<400> SEQUENCE: 1

Cys Glu Xaa Gly Xaa Xaa Xaa Xaa Cys
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide EE-2

<400> SEQUENCE: 2

Ala Cys Glu Met Gly Phe Phe Gln Asp Cys Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide EE-12

<400> SEQUENCE: 3

Cys Glu Met Gly Phe Phe Gln Asp Cys Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide EE-2F

<400> SEQUENCE: 4

Ala Cys Glu Met Gly Phe Phe Ala Asp Cys Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide EE-39

<400> SEQUENCE: 5

Ala Cys Glu Met Gly Phe Phe Lys Asp Cys Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide EE-41

<400> SEQUENCE: 6

Ala Cys Glu Met Gly Phe Phe Leu Asp Cys Gly
1               5                   10
```

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide EE-44

<400> SEQUENCE: 7

Cys Glu Met Gly Phe Phe Ala Asp Cys
1               5

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide FAM labelled tracer peptide

<400> SEQUENCE: 8

Lys Lys Arg Tyr Ser Arg Asp Phe Leu Leu Ala Leu Gln Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide phage display peptide
<220> FEATURE:
<221> NAME/KEY: MISC_FEATURE
<222> LOCATION: (3)..(9)
<223> OTHER INFORMATION: Xaa can be any naturally occuring,
      non-naturally occuring or synthetic amino acid

<400> SEQUENCE: 9

Ala Cys Xaa Xaa Xaa Xaa Xaa Xaa Xaa Cys Gly Gly Gly Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide PHAGESOL

<400> SEQUENCE: 10

Lys Lys Arg Tyr Ser Arg Asp Gln Leu Val Ala Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide C-E-(T/M/L)-G-F-F-X-X-C
<220> FEATURE:
<221> NAME/KEY: MISC_FEATURE
<222> LOCATION: (3)..(3)
<223> OTHER INFORMATION: Xaa can be Threonine, Methionine or Leucine
<220> FEATURE:
<221> NAME/KEY: MISC_FEATURE
<222> LOCATION: (7)..(8)
<223> OTHER INFORMATION: Xaa can be any naturally occuring,
      non-naturally occuring or synthetic amino acid

<400> SEQUENCE: 11

Cys Glu Xaa Gly Phe Phe Xaa Xaa Cys
1               5

```
<210> SEQ ID NO 12
<211> LENGTH: 7
<212> TYPE: PRT
<213> ORGANISM: Artificial Sequence
<220> FEATURE:
<223> OTHER INFORMATION: Synthetic peptide eIF4E interaction binding
      motif
<220> FEATURE:
<221> NAME/KEY: MISC_FEATURE
<222> LOCATION: (2)..(2)
<223> OTHER INFORMATION: Xaa can be any naturally occuring,
      non-naturally occuring or synthetic amino acid
<220> FEATURE:
<221> NAME/KEY: MISC_FEATURE
<222> LOCATION: (4)..(5)
<223> OTHER INFORMATION: Xaa can be any naturally occuring,
      non-naturally occuring or synthetic amino acid
<220> FEATURE:
<221> NAME/KEY: MISC_FEATURE
<222> LOCATION: (7)..(7)
<223> OTHER INFORMATION: Xaa can be any hydrophobic amino acid

<400> SEQUENCE: 12

Tyr Xaa Arg Xaa Xaa Leu Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide CEXGFFXXC
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 13

Cys Glu Xaa Gly Xaa Xaa Xaa Xaa Cys
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide EE-2A

<400> SEQUENCE: 14

Ala Cys Ala Met Gly Phe Phe Gln Asp Cys Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide EE-2B

<400> SEQUENCE: 15

Ala Cys Glu Ala Gly Phe Phe Gln Asp Cys Gly
1               5                   10

<210> SEQ ID NO 16
<211> LENGTH: 11
```

```
<212> TYPE: PRT
<213> ORGANISM: Artificial Sequence
<220> FEATURE:
<223> OTHER INFORMATION: Synthetic peptide EE-2C

<400> SEQUENCE: 16

Ala Cys Glu Met Ala Phe Phe Gln Asp Cys Gly
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide EE-2D

<400> SEQUENCE: 17

Ala Cys Glu Met Gly Ala Phe Gln Asp Cys Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide EE-2E

<400> SEQUENCE: 18

Ala Cys Glu Met Gly Phe Ala Gln Asp Cys Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide EE-2G

<400> SEQUENCE: 19

Ala Cys Glu Met Gly Phe Phe Gln Ala Cys Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide EE-19

<400> SEQUENCE: 20

Ala Cys Asp Met Gly Phe Phe Gln Asp Cys Gly
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide EE-20

<400> SEQUENCE: 21

Ala Cys Glu Ile Gly Phe Phe Gln Asp Cys Gly
1               5                   10

<210> SEQ ID NO 22
<211> LENGTH: 11
<212> TYPE: PRT
```

```
<213> ORGANISM: Artificial Sequence
<220> FEATURE:
<223> OTHER INFORMATION: Synthetic peptide EE-21

<400> SEQUENCE: 22

Ala Cys Glu Leu Gly Phe Phe Gln Asp Cys Gly
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide EE-22
<220> FEATURE:
<221> NAME/KEY: MOD_RES
<222> LOCATION: (4)..(4)
<223> OTHER INFORMATION: Nle

<400> SEQUENCE: 23

Ala Cys Glu Leu Gly Phe Phe Gln Asp Cys Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide EE-23
<220> FEATURE:
<221> NAME/KEY: MISC_FEATURE
<222> LOCATION: (4)..(4)
<223> OTHER INFORMATION: cyclobutylalanine

<400> SEQUENCE: 24

Ala Cys Glu Ala Gly Phe Phe Gln Asp Cys Gly
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide EE-27
<220> FEATURE:
<221> NAME/KEY: MOD_RES
<222> LOCATION: (5)..(5)
<223> OTHER INFORMATION: bAla

<400> SEQUENCE: 25

Ala Cys Glu Met Ala Phe Phe Gln Asp Cys Gly
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide EE-28
<220> FEATURE:
<221> NAME/KEY: MOD_RES
<222> LOCATION: (5)..(5)
<223> OTHER INFORMATION: METHYLATION OF GLYCINE TO SARCOSINE

<400> SEQUENCE: 26

Ala Cys Glu Met Gly Phe Phe Gln Asp Cys Gly
1               5                   10

<210> SEQ ID NO 27
```

```
<211> LENGTH: 11
<212> TYPE: PRT
<213> ORGANISM: Artificial Sequence
<220> FEATURE:
<223> OTHER INFORMATION: Synthetic peptide EE-29

<400> SEQUENCE: 27

Ala Cys Glu Met Pro Phe Phe Gln Asp Cys Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide EE-30

<400> SEQUENCE: 28

Ala Cys Glu Met Gly Tyr Phe Gln Asp Cys Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide EE-31

<400> SEQUENCE: 29

Ala Cys Glu Met Gly Trp Phe Gln Asp Cys Gly
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide EE-33

<400> SEQUENCE: 30

Ala Cys Glu Met Gly Leu Phe Gln Asp Cys Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide EE-34

<400> SEQUENCE: 31

Ala Cys Glu Met Gly Phe Leu Gln Asp Cys Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide EE-35

<400> SEQUENCE: 32

Ala Cys Glu Met Gly Phe Tyr Gln Asp Cys Gly
1               5                   10

<210> SEQ ID NO 33
<211> LENGTH: 11
```

```
<212> TYPE: PRT
<213> ORGANISM: Artificial Sequence
<220> FEATURE:
<223> OTHER INFORMATION: Synthetic peptide EE-36

<400> SEQUENCE: 33

Ala Cys Glu Met Gly Phe Trp Gln Asp Cys Gly
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide EE-37

<400> SEQUENCE: 34

Ala Cys Glu Met Gly Tyr Tyr Gln Asp Cys Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic peptide EE-38

<400> SEQUENCE: 35

Ala Cys Glu Met Gly Leu Leu Gln Asp Cys Gly
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic peptide EE-40

<400> SEQUENCE: 36

Ala Cys Glu Met Gly Phe Phe Gly Asp Cys Gly
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide biotin-labelled peptide

<400> SEQUENCE: 37

Leu Pro Glu Thr Gly Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide EE-2H

<400> SEQUENCE: 38

Cys Glu Met Gly Phe Phe Gln Asp Cys
1               5

<210> SEQ ID NO 39
<211> LENGTH: 11
<212> TYPE: PRT
```

<213> ORGANISM: Artificial Sequence
<220> FEATURE:
<223> OTHER INFORMATION: Synthetic peptide EE-1

<400> SEQUENCE: 39

Ala Cys Glu Thr Gly Phe Phe Thr Gly Cys Gly
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide EE-3

<400> SEQUENCE: 40

Ala Cys Glu Leu Gly Tyr Tyr Asn Asp Cys Gly
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic peptide EE-4

<400> SEQUENCE: 41

Ala Cys Glu Thr Gly Phe Phe Leu Lys Cys Gly
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide EE-5

<400> SEQUENCE: 42

Ala Cys Glu Leu Gly Phe Tyr Arg Leu Cys Gly
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide EE-6

<400> SEQUENCE: 43

Ala Cys Glu Thr Gly Phe Phe Leu Arg Cys Gly
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide EE-7

<400> SEQUENCE: 44

Ala Cys Glu Thr Gly Tyr Phe Ser Gln Cys Gly
1               5                   10

<210> SEQ ID NO 45
<211> LENGTH: 11
<212> TYPE: PRT
<213> ORGANISM: Artificial Sequence

```
<220> FEATURE:
<223> OTHER INFORMATION: Synthetic peptide Peptide 45

<400> SEQUENCE: 45

Ala Cys Ile His Ser Pro Thr Ser Leu Cys Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic peptide EE-8

<400> SEQUENCE: 46

Ala Cys Glu Thr Gly Phe Tyr Lys Thr Cys Gly
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide EE-9

<400> SEQUENCE: 47

Ala Cys Glu Met Gly Tyr Phe Gly Asn Cys Gly
1               5                   10
```

UNITED STATES PATENT AND TRADEMARK OFFICE
CERTIFICATE OF CORRECTION

PATENT NO. : 12,338,296 B2  Page 1 of 1
APPLICATION NO. : 17/436118
DATED : June 24, 2025
INVENTOR(S) : Simon Ng et al.

It is certified that error appears in the above-identified patent and that said Letters Patent is hereby corrected as shown below:

In the Claims

At Column 39, Line 34, "CEX1GX2X3X4X5C" should be -- $CEX_1GX_2X_3X_4X_5C$ --.

At Column 39, Line 51, "(e1F4E);" should be -- (eIF4E); --.

At Column 39, Line 56, "e1F4E" should be -- eIF4E --.

At Column 39, Line 58, "e1F4E" should be -- eIF4E --.

At Column 39, Line 58, "e1F4E" should be -- eIF4E --.

At Column 39, Line 60, "e1F4E" should be -- eIF4E --.

Signed and Sealed this
Tenth Day of February, 2026

John A. Squires
*Director of the United States Patent and Trademark Office*